United States Patent
Rathore et al.

(10) Patent No.: US 11,147,929 B2
(45) Date of Patent: Oct. 19, 2021

(54) FLUID COLLECTOR

(71) Applicants: Jai Hind Rathore, Moradabad (IN);
Bharati Rathore, Moradabad (IN);
Pratibha Rathore, Moradabad (IN);
Neelam Rathore, Moradabad (IN);
Bhuvan Chandra Rathore, Moradabad (IN)

(72) Inventors: Jai Hind Rathore, Moradabad (IN);
Bharati Rathore, Moradabad (IN);
Pratibha Rathore, Moradabad (IN);
Neelam Rathore, Moradabad (IN);
Bhuvan Chandra Rathore, Moradabad (IN)

(*) Notice: Subject to any disclaimer, the term of this patent is extended or adjusted under 35 U.S.C. 154(b) by 42 days.

(21) Appl. No.: 16/817,835

(22) Filed: Mar. 13, 2020

(65) Prior Publication Data
US 2020/0222641 A1 Jul. 16, 2020

Related U.S. Application Data

(62) Division of application No. 15/552,014, filed as application No. PCT/IB2016/051060 on Feb. 26, 2016, now Pat. No. 10,729,857.

(30) Foreign Application Priority Data

Mar. 10, 2015 (IN) .............................. 645/Del/2015
Jan. 28, 2016 (IN) ............................. 201611002989

(51) Int. Cl.
*A61M 5/32* (2006.01)
*A61M 5/24* (2006.01)
*A61M 5/50* (2006.01)

(52) U.S. Cl.
CPC ............ *A61M 5/3234* (2013.01); *A61M 5/24* (2013.01); *A61M 5/50* (2013.01); *A61M 5/3202* (2013.01);
(Continued)

(58) Field of Classification Search
CPC ........ A61M 5/3234; A61M 5/24; A61M 5/50; A61M 5/3202; A61M 5/322; A61M 5/28; A61M 5/281; A61M 5/5066; A61M 5/315; A61M 5/31511; A61M 5/31515; A61M 5/3221; A61M 5/3232; A61M 2005/3235;
(Continued)

(56) References Cited

U.S. PATENT DOCUMENTS 3,810,391 A * 5/1974 Suovaniemi .......... A61M 5/315
73/864.18
4,312,344 A * 1/1982 Nilson ............... A61M 5/31511
604/212
2014/0276451 A1* 9/2014 Cowan .................. A61M 5/007
604/218

* cited by examiner

*Primary Examiner* — Kevin C Sirmons
*Assistant Examiner* — Antarius S Daniel
(74) *Attorney, Agent, or Firm* — BakerHostetler

(57) ABSTRACT

Embodiments of the preset invention provide a fluid collector configured to releasably engage with an injector. The fluid collector comprises a fluid container configured to have a centrally extended conical projection containing a detachable needle holder at a proximal end of said conical projection to hold a detachable hypodermic needle, a piston assembly having a piston flange provided with a conical cavity at center of said piston assembly at a distal end of said piston assembly to couple said plunger shaft of said injector and a container cover being internally provided with a concave diaphragm having a central hole to allow entry of said detachable hypodermic needle along with a detachable needle hub.

8 Claims, 38 Drawing Sheets

A

200

(52) U.S. Cl.
CPC ............... *A61M 2005/2492* (2013.01); *A61M 2005/3242* (2013.01); *A61M 2205/273* (2013.01)

(58) Field of Classification Search
CPC .. A61M 2005/3239; A61M 2005/3242; A61M 2005/2492; A61M 2005/323; A61M 2005/3142; A61M 2005/3236; A61M 2005/3241; A61M 2205/273; A61B 5/150267; A61B 5/150099; A61B 5/1416; A61B 5/1405; A61B 5/15; A61J 1/05; A61J 1/06

See application file for complete search history.

FLUID COLLECTOR

CROSS REFERENCE TO RELATED APPLICATION

This application is a divisional application of the U.S. patent application Ser. No. 15/552,014 filed Aug. 18, 2017, entitled "A FLUID INJECTING SYSTEM WITH NEEDLE RETRACTION BY VACUUM," which is a national stage entry of PCT/IB2016/051060 filed Feb. 26, 2016, which claims priority to Indian patent application no. 645/Del/2015 filed Mar. 10, 2015 and Indian patent application no. 201611002989 filed Jan. 28, 2016, the contents of which are incorporated by reference in their entireties.

FIELD OF THE INVENTION

Embodiments of the present invention relate to hypodermic syringes and more particularly to a fluid injecting system and a method thereof. Further, the fluid injecting system is having an injector and a fluid-cartridge. Also, the system prevents from needle stick injuries and is economical and user friendly.

BACKGROUND OF THE INVENTION

Hypodermic syringes having retractable needles are well-known in the art. These syringes are commonly used in healthcare industry to inject therapeutics below the skin of patients. Despite their utility, the hypodermic syringes pose significant safety risks to medical professionals, patients, children playing in a park, street walkers and anyone who could accidentally be pricked by exposed needle of the hypodermic syringe. After disposal, needle stick injuries resulting from contact with discarded needles are an increasing problem. The needle-stick injury is a percutaneous wound typically set by a needle-point before and after use. These events of occupational health hazards are of great concern because of the risk of transmitting blood-borne diseases through passage of hepatitis B virus (HBV), hepatitis C virus (HCV), Human Immunodeficiency Virus (HIV) and the like. Disposal of bio-medical waste also poses a large public health concern. As a result of the foregoing concerns, the safe fluid injecting systems are gaining more and more attention to avoid dangerous needle prick injuries.

Generally, an injectable drug (the fluid) is stored, packed and supplied conveniently by pharmaceutical industries in vials, ampoules and the like containers, which need hypodermic syringes to inject it into the body of human beings or animals. In conventional syringes, an operator first transfers a required volume of the drug into an empty hypodermic syringe by aspiration through the needle before injecting into the patient's body. In case of retractable syringes, a retraction mechanism operable on spring or a similar biasing means is activated to retract the needle into the barrel. After completion of an injection process, the empty vials, ampoules or container, the used hypodermic syringe along with their packaging material etc., which is generally made of non-biodegradable plastic, is finally disposed-off as bio-medical waste, adversely poses a considerable economic as well as environmental burden.

It is also important to note that the injectable drug packed by pharmaceutical industries is never filled into such containers up to the brim but approximately 20-40% volume of air always remains available in direct contact with packed drug during the entire course of storage. The oxygen, nitrogen and other active molecules present in such entrapped air also keep on interacting continuously with the molecules of drug contents, consequently a negative impact on the drug contents leading to ultimate decrease in the efficacy of drug may not be completely ruled out. On the other hand, before aspirating drug content into an empty syringe, the user first injects a current of air through hypodermic needle of empty syringe into such container in order to increase the pressure of air on the drug content, so that it may easily be aspirated into empty syringe by application of negative pressure. The air current forcibly injected into the drug may not be ruled out to contain harmful bio-active molecules or other pollutants except the normal ingredients of air like nitrogen, oxygen, carbon-di-oxide etc. The forceful current of such contaminated air pressed into injectable drug contents increases the probability of chemical interaction between such air and the drug contents to maximum extent due to dissolution of a considerable amount of air contents into drug contents at such high pressure. Under such circumstances, the adverse effect on the potency and efficacy of drug may also not be ruled out. Besides, such current of air passed into the drug contents at such higher pressure is also bound to generate millions of bubbles/ micro-bubbles of entrapped polluted air, which are aspirated into the empty syringe. The user may, however, take care of visible bubbles of air but he may never avoid the millions of micro-bubbles entering directly into the blood stream of patient and posing adverse/undesirable impact on patient. We, however, could not find any discussions/literature on these issues, but these issues may not be neglected and need be effectively addressed. We strongly advocate that the injectable drug contents should never come in contact of air contents at any time and the drug need be injected directly into the patient without its being transferred into any other container like empty syringe, so that the potency of drug contents may be maintained and guarded zealously, right from the stage of manufacturing up to its administration into the patient's body.

There have been a number of solutions provided for efficient hypodermic syringes with retractable needles and few of them have been discussed below:

US20060264840A1 describes a retractable needle safety syringe. The syringe comprises a syringe body, a syringe cavity, a plunger, a variable vacuum compartment, a shaft brake, and a ram member. The plunger assembly includes a plunger shaft and a piston slidably engaged within the syringe body. The variable vacuum compartment being operative to provide a vacuum force on the plunger shaft directed from a bottom syringe body end toward a top syringe body end. The shaft brake being operative to frictionally engage the plunger shaft to provide first and second frictional forces in opposition to the vacuum force, the first frictional force being exerted prior to the piston reaching the bottom syringe body end, the second frictional force being exerted in response to the engagement of the ram member with the shaft brake. Further, the second frictional force is less than the first frictional force.

U.S. Pat. No. 6,712,787B1 describes a retractable safety syringe. The retractable safety syringe retracts a needle cannula into a plunger module and thus prevents reuse or an accidental needle prick by destroying a plunger barrier and a cannula barrier within the syringe. Further, the needle cannula is released into the plunger module by shearing the cannula barrier and the plunger barrier with an internal annular shear and cutter head.

U.S. Pat. No. 9,097,435B2 describes a retractable needle fluid transfer device. The device includes a manually operable actuator. Upon depressing the actuator, a spring displaces a needle rearwardly to enclose a contaminated needle. The device includes forward and rearward stops for impeding displacement of the needle after the needle is retracted. A safety sampling access port adapter for obtaining fluid samples from a fluid line is also disclosed. The sampling adapter includes a collapsible socket configured to cooperate with a fluid container such as a vacuum tube. Further, a needle assembly is provided to pierce a seal on the fluid container. After use, the socket is collapsed to prevent contact with the contaminated needle.

The aforesaid documents and other similar solutions may strive to provide efficient hypodermic syringes with retractable needles; however, they still have a number of limitations and shortcomings such as, but not limited to, relatively low reliability and relatively high complexity as well as relatively high manufacturing cost. Another disadvantage of these hypodermic syringes is the inability to evacuate the entire contents of the injectable drug from cavity. Further, these syringes are not economically feasible because incorporation of a needle retraction mechanism (NRM) in the hypodermic syringes enhances overall cost of the hypodermic syringes to such a greater extent that they become beyond reach of general masses. Furthermore, the operation of safety features is not self-evident and therefore additional training is required to use the hypodermic syringes effectively. Also, the existing hypodermic syringes require exertion of additional force to activate the needle retraction mechanism after the injection process, which ultimately becomes optional to the operator. The forceful activation of the needle retraction mechanism also leads to back stroke and becomes painful for the patient as well as the healthcare practitioners. As a result of the back stroke, the needle shakes and damages tissues which may result in bleeding and abscess may also occur due to the tissue injury.

In addition, the existing hypodermic syringes include a needle which is retracted into a barrel under action of a spring after the injection process. However, in such kind of the hypodermic syringes, the needle is retracted too fast which may result in bursting out of blood under body pressure from punctured hole on the body, which further brings secondary cross infections. The conventional hypodermic syringes also lack full-proof locking arrangement as well as effective retraction mechanism to prevent and restrict further use of the hypodermic syringes once used. Also, these hypodermic syringes do not include a fluid collecting device for collecting a fluid.

In order to effectively address the existing problems and shortcomings, there remains a constant need in the art for an efficient fluid injecting system and a method thereof, for safely injecting a fluid without any risk of needle stick injury. Further, we need such a fluid injecting system capable of not merely retracting the hypodermic needle following its use, but also capable of capturing and firmly retaining the used hypodermic needle in the retracted position within the system rendering it non-reusable. The proposed fluid injecting system not only addresses all such known alarming issues effectively, but also provides a clean, green, cheap, user-friendly and reliable technological advancement over the known alternatives.

OBJECT OF THE INVENTION

An object of the present invention is to provide a fluid injecting system having an injector and a fluid-cartridge.

Another object of the present invention is to provide a fluid injecting system having an injector and a fluid collector.

Another object of the present invention is to provide the fluid-cartridge to replace the conventional packaging drug containers i.e. vials, ampoules and the like containers, conventionally used by pharmaceutical industries to pack and store the injectable fluid.

Another object of the present invention is to make the fluid-cartridge an integral part of the fluid injecting system by using it to replace the barrel of the conventional syringe.

Another object of the present invention is to provide the fluid-cartridge, which comprises of pre-defined volume of fluid.

Another object of the present invention is to provide the fluid-cartridge having retractable needle assembly either containing inbuilt or replaceable hypodermic needle or has provision to attach the hypodermic needle of desired dimensions.

Another object of the present invention is to provide the fluid-cartridge, wherein inbuilt hypodermic needle is either encapsulated inside the cartridge and is exposed at the time of injection process, or inbuilt hypodermic needle is safely guarded by needle guard out the fluid-cartridge.

Another object of the present invention is to provide the fluid-cartridge having the piston assembly with means to dislodge the retractable needle from its own engagement means and engage itself with the retractable needle assembly to retain it after the completion of the injection process.

Another object of the present invention is to provide the fluid-cartridge having the piston assembly with means to engage with plunger shaft of the injector, which may axially move the piston assembly in forward and backward directions.

Another object of the present invention is to provide the fluid-cartridge having a fluid container with engagement means to axially engage/attach with the injector to constitute the fluid injecting system.

Another object of the present invention is to provide the fluid injecting system comprising the injector having attachments means at its proximal end to firmly attach with the fluid-cartridge during the injection process.

Another object of the present invention is to provide the fluid injecting system comprising the injector wherein the plunger assembly consisting of inner and outer plunger barrels wherein the substantial withdrawal of outer plunger barrel generates a vacuum between the two plunger barrels and unite them to constitute a single plunger unit by activating locking means provided with the inner plunger barrel.

Another object of the present invention is to provide the fluid injecting system with the injector wherein the inner plunger barrel is axially coupled with a plunger shaft at its proximal end, which at proximal end is provided with means to attach with piston assembly of fluid-cartridge during the injection process.

Another object of the present invention is to provide the fluid injecting system with the injector wherein assembly of plunger barrel is provided with a locking means, which operate to lock the outer plunger barrel with the inner plunger barrel on the substantial withdrawal of outer plunger assembly in backward direction to generate a vacuum between the two barrels.

Another object of the present invention is to provide the fluid injecting system with the injector wherein the locking means provided with plunger assembly is unlocked when the locked and united plunger barrel is substantially pushed into the injector. This unlocking action releases the vacuum between the two barrels in order to fold the barrels and to bring the inner plunger barrel in original state inside the outer plunger barrel.

Another object of the present invention is to provide the fluid injecting system with the injector, wherein the plunger shaft axially attached at the proximal end of the inner plunger barrel and is provided with a locking means to attach firmly with the piston assembly of fluid-cartridge at its distal end during the injection process and detach automatically after the completion of injection process.

Another object of the present invention is to provide the fluid injecting system with the injector, wherein the plunger shaft first interlocks with the piston assembly and then pushes it in forward direction to inject the fluid of the fluid-cartridge into patient and when the last drop is injected, it withdraws automatically the piston assembly in backward direction along with the retractable needle assembly coupled with hypodermic needle after the completion of injection process without intervention of user and thereafter automatically detach itself from the piston assembly to release empty fluid-cartridge.

Another object of the present invention is to provide the fluid injecting system with the injector, wherein the plunger shaft moves the piston assembly in forward direction when the locked and united plunger barrels is pushed in forward direction but the plunger shaft retracts automatically in backward direction due to unlocking of plunger barrels and release of vacuum when the locked united plunger barrel is completely pushed onto the injector.

Another object of the present invention is to provide the fluid injecting system with the fluid collector which is configured to collect a fluid from a target and is removably connected with the injector.

Another object of the present invention is to provide a fluid injecting method for safely injecting the fluid at the injectable site without any risk of needle stick injury.

Another object of the present invention is to provide a fluid collecting method for collecting the fluid from the target.

SUMMARY OF THE INVENTION

Embodiments of the present invention aim to provide a fluid injecting system and a method thereof. The fluid injecting system is having an injector and a fluid-cartridge and is capable of retracting a hypodermic needle by virtue of self-generated vacuum and encapsulates the hypodermic needle in retracted position within the fluid-cartridge after completion of an injection process. The fluid injecting system completely prevents risk of needle stick injuries as the fluid-cartridge encapsulating the retracted needle becomes non-reusable. Further, the injector of the fluid injecting system is reusable, which may be used repeatedly in combination with the fluid-cartridge. In addition, the fluid injecting system is economical and user friendly. Also, the present invention provides a fluid collector.

In accordance with an embodiment of the present invention, the fluid injecting system comprising an injector having an injector body, a plunger shaft, a plunger assembly having an inner plunger barrel slidable within an outer plunger barrel, the inner plunger barrel having a locking means configured to restrict movement of the outer plunger barrel in forward direction, the outer plunger barrel and the inner plunger barrel are configured to form a united plunger barrel when the outer plunger barrel is pulled out at its full length, and a fluid-cartridge having injectable fluid packed between piston assembly and retractable needle assembly with (or without) a hypodermic needle for injecting the fluid at an injectable site. The fluid-cartridge is configured to releasably engage with the injector at a proximal end of the injector.

Further, a vacuum is created between the outer plunger barrel and the inner plunger barrel upon formation of the united plunger barrel. Also, forward movement of the united plunger barrel transfers the fluid from the fluid-cartridge into the injectable site. The hypodermic needle retracts within empty fluid-cartridge due to release of the vacuum and the injector is disengaged from the fluid-cartridge for reuse.

In accordance with an embodiment of the present invention, the injector body comprises a partition ring and a flange ring at a proximal end of the injector body to hold the plunger shaft in center of the injector body. Further, the injector body comprises a finger flange at a distal end of the injector body for holding the injector and an inner engagement means and an outer engagement means at the proximal end of the injector body to engage the fluid-cartridge. Preferably, the inner engagement means and the outer engagement means are, but not limited to, L-shaped grooves.

In accordance with an embodiment of the present invention, the outer plunger barrel of the plunger assembly comprises a thumb-rest at a distal end and an interiorly protruded flange rim at a proximal end of the outer plunger barrel. Further, the thumb-rest is having a rubber O-ring.

In accordance with an embodiment of the present invention, the interiorly protruded flange rim is having an inner diameter equal to an outer diameter of the inner plunger barrel of the plunger assembly. Further, the outer plunger barrel of the plunger assembly is having an outer diameter equal to an inner diameter of the injector body.

In accordance with an embodiment of the present invention, the inner plunger barrel of the plunger assembly comprises a piston holder at a distal end of the inner plunger barrel of the plunger assembly to hold a piston seal between exterior of the inner plunger barrel and interior of the outer plunger barrel.

In accordance with an embodiment of the present invention, the plunger shaft is configured to have an axially furrowed forceps-lock head containing two outwardly protruded flaps. Further, the two outwardly protruded flaps are configured to be sharp-edged blades at a proximal end of the flaps.

In accordance with an embodiment of the present invention, the plunger shaft is a needle shaped plunger shaft.

In accordance with an embodiment of the present invention, the locking means is housed inside the inner plunger barrel. Further, the locking means is having a conical lock-notch which protrudes out through a longitudinal slot provided at the inner plunger barrel. Also, the locking means is, but not limited to, U-clip locking means.

In accordance with an embodiment of the present invention, the plunger assembly is housed inside a distal chamber of the injector and the plunger shaft is housed axially at center of a proximal chamber of the injector.

In accordance with an embodiment of the present invention, the plunger assembly is configured to have a first spring. Further, the first spring is provided between exterior of the inner plunger barrel and interior of the outer plunger barrel of the plunger assembly.

In accordance with an embodiment of the present invention, the inner plunger barrel is provided with plurality of button cells and a LED indicator. Further, the inner plunger barrel is provided with a plurality of intrusions to hold a plurality of metallic strips to form a LED circuit.

In accordance with an embodiment of the present invention, the injector is configured to have a push-button provided at a septum at the proximal end of the injector. Preferably, the push-button is provided with a second spring.

In accordance with an embodiment of the present invention, the fluid is an injectable fluid.

In accordance with an embodiment of the present invention, the fluid-cartridge further comprises a fluid container having a distal end and a proximal end and configured to contain the fluid, a piston assembly having a piston flange and a conical cavity configured to engage the plunger shaft, a retractable needle assembly having a needle hub configured to hold the hypodermic needle, a needle holder configured to hold the needle hub, an O-ring, a cap having a plurality of horizontally extended pins towards the distal end of the fluid container and a needle guard configured to cover the hypodermic needle disposed inside the fluid container. The fluid container comprises engagement means at the distal end of the fluid container to couple with the injector body. Further, the proximal end of the fluid container is provided with a centrally opened conical mouth to hold the needle hub. The plurality of horizontally extended pins of the cap is configured to pass through a plurality of clefts of the O-ring to slidably hold the O-ring. Also, the cap is configured to hold the needle holder. The needle guard is drawn out by a user allowing the hypodermic needle along with the needle guard to extend out of the needle holder. The united plunger barrel of the injector is pushed in forward direction to couple or interlock the plunger shaft with the conical cavity of the piston assembly forming a single plunger unit. The single plunger unit exerts a downward pressure on the fluid for injecting the fluid through the hypodermic needle at the injectable site and the single plunger unit also exerts a downward pressure on the plurality of horizontally extended pins of the cap for injecting the remaining fluid at the injectable site and releasing the needle holder along with the hypodermic needle.

In accordance with an embodiment of the present invention, the engagement means are, but not limited to, protrusions provided at both interior and exterior of the fluid container.

In accordance with an embodiment of the present invention, the piston flange is configured to have a needle catch projection at center of the piston assembly at a proximal end of the piston assembly. Further, the needle catch projection is configured to have a conical ridge at a proximal end of the needle catch projection.

In accordance with an embodiment of the present invention, the needle catch projection is configured to have, but not limited to, a longitudinal furrow or a conical groove at surface of the needle catch projection.

In accordance with an embodiment of the present invention, the piston flange is configured to have plurality of grooves to hold a piston seal between the piston flange and the fluid container.

In accordance with an embodiment of the present invention, the needle hub comprises of a conical cavity at a distal end of the needle hub to couple with the piston assembly. Further, the needle hub holds the hypodermic needle at center position at a proximal end of the needle hub. Also, the needle hub is configured to have a conical ridge at the proximal end of the needle hub.

In accordance with an embodiment of the present invention, the needle holder is configured to have a conical cavity with a conical groove at a proximal end of the needle holder.

In accordance with an embodiment of the present invention, the needle holder and the needle hub are configured to fuse together.

In accordance with an embodiment of the present invention, the needle guard is configured to cover the hypodermic needle using a locking means. Further, the needle guard is configured to have a knob like structure at a proximal end of the needle guard.

In accordance with an embodiment of the present invention, the needle guard is rotated in an anti-clockwise direction at a predetermined angle and drawn to separate from the hypodermic needle. Further, the predetermined angle is 90°.

In accordance with an embodiment of the present invention, the needle guard is having an outer diameter equal to the centrally opened conical mouth of the fluid container.

In accordance with an embodiment of the present invention, the fluid container is configured to have a rubber cap at the distal end of the fluid container.

In accordance with an embodiment of the present invention, the piston assembly is configured to have a cylindrical saw blade.

In accordance with an embodiment of the present invention, the retractable needle assembly is configured to have a thin layer circular diaphragm between the O-ring and the needle holder.

In accordance with an embodiment of the present invention, the piston flange is configured to have a circular ridge projection at a proximal end of the piston flange.

In accordance with an embodiment of the present invention, the needle holder of the retractable needle assembly is configured to have a flange rim with a collar projection at a distal end of the needle holder for holding the O-ring. Further, the O-ring is having an inner diameter at a proximal end of the O-ring greater than an inner diameter of the O-ring at a distal end of the O-ring to engage the O-ring around the collar projection.

In accordance with an embodiment of the present invention, the hypodermic needle extends out of the centrally open conical mouth due to pressure exerted on the united plunger barrel.

In accordance with an embodiment of the present invention, the fluid is sandwiched between the piston assembly and the retractable needle assembly.

In accordance with an embodiment of the present invention, the fluid collector configured to releasably engage with the injector comprising a fluid container configured to have a centrally extended conical projection containing a detachable needle holder at a proximal end of the conical projection to hold a detachable hypodermic needle, a piston assembly having a piston flange provided with a conical cavity at center of the piston assembly at a distal end of the piston assembly to couple with the plunger shaft of the injector, a container cover being internally provided with a concave diaphragm having a central hole to allow entry of the detachable hypodermic needle along with a detachable needle hub. The container cover is removably attached with the fluid container. Further, the fluid container is provided with engagement means at the distal end to engage with the injector body. The united plunger barrel of the injector retaining the vacuum is pushed completely in forward direction to attach the plunger shaft with the conical cavity of the piston assembly. Further, release of the vacuum results in backward movement of the inner plunger barrel of the united plunger barrel along with the piston assembly, which finally results in suction of a fluid from the intended target into the fluid container.

In accordance with an embodiment of the present invention, the fluid container comprises a thin layer of diaphragm at a distal end of the fluid container.

In accordance with an embodiment of the present invention, the piston flange is configured to have a plurality of grooves to hold a piston seal between the piston flange and the fluid container.

In accordance with an embodiment of the present invention, the container cover is having an internal diameter higher than an outer diameter of the fluid container at a proximal end of the fluid container to attach with the fluid container. Further, the container cover is attached with the fluid container by way of a removable ring seal to cover the proximal end of the fluid container.

In accordance with an embodiment of the present invention, the concave diaphragm is provided in middle of the container cover.

In accordance with an embodiment of the present invention, the central hole is configured to have a diameter lesser than the detachable needle hub.

In accordance with an embodiment of the present invention, the concave diaphragm is divided into a plurality of equal parts which are configured to be pressed only towards bottom of the container cover to increase size of the central hole to allow entry of the detachable hypodermic needle along with the detachable needle hub.

In accordance with an embodiment of the present invention, the fluid injecting method comprising the steps of providing a fluid-cartridge having a fluid sandwiched between a piston assembly and a retractable needle assembly of the fluid-cartridge, reversibly coupling the fluid-cartridge with an injector having a plunger shaft and a united plunger barrel and pushing the united plunger barrel in a forward direction to deliver the fluid from the fluid-cartridge into an injectable site.

In accordance with an embodiment of the present invention, the injector having an inner plunger barrel slidable within an outer plunger barrel and the united plunger barrel is formed by pulling out the outer plunger barrel completely. Further, the united plunger barrel is configured to retain a vacuum between the inner plunger barrel and the outer plunger barrel.

In accordance with an embodiment of the present invention, the injector is configured for actuating an axial movement of the plunger shaft in the forward direction and in a backward direction for retracting the plunger shaft.

In accordance with an embodiment of the present invention, the fluid is an injectable fluid.

In accordance with an embodiment of the present invention, the fluid-cartridge is reversibly coupled with the injector at a proximal end of the injector.

In accordance with an embodiment of the present invention, the fluid collecting method comprising the steps of providing a fluid collector having a piston assembly and a detachable hypodermic needle covered by a container cover, reversibly coupling the fluid collector with an injector having a plunger shaft and a united plunger barrel, removing the container cover from the fluid collector to expose the detachable hypodermic needle, inserting the detachable hypodermic needle into a target fluid source and collecting a fluid from the target fluid source into the fluid collector.

In accordance with an embodiment of the present invention, the step of inserting further comprises a step of pushing the united plunger barrel in a forward direction to attach the plunger shaft of the injector with the piston assembly of the fluid collector.

In accordance with an embodiment of the present invention, the injector having an inner plunger barrel slidable within an outer plunger barrel and the united plunger barrel is formed by pulling out the outer plunger barrel completely. Further, the united plunger barrel is configured to retain a vacuum between the inner plunger barrel and the outer plunger barrel.

In accordance with an embodiment of the present invention, the injector is configured for actuating an axial movement of the plunger shaft in a forward direction and in a backward direction for retracting the plunger shaft.

In accordance with an embodiment of the present invention, the fluid collector is reversibly coupled with the injector at a proximal end of the injector.

BRIEF DESCRIPTION OF THE ACCOMPANYING DRAWINGS

The manner, in which the above-recited features of the present invention may be understood in detail, more particular description of the invention briefly summarized above, have been referred by the embodiments, some of which are illustrated in the appended drawings. It may, however, be noted, that the drawings appended herein illustrate only typical embodiments of this invention and are therefore not to be considered limiting of its scope, for the invention may admit to other equally effective embodiments.

These and other features, benefits and advantages of the present invention will become apparent by reference to the following text figure, with like reference numbers referring to like structures across the views, wherein.

FIGS. 4(a), (a'), (b), (b'), (c) and (c') illustrate various types of the fluid-cartridges having a needle retraction mechanism in accordance with an embodiment of the present invention.

FIGS. 5(a), (a'), (b), (b'), (c) and (c') illustrate various types of the fluid-cartridges having another needle retraction mechanism in accordance with another embodiment of the present invention.

FIGS. 6(a), (a'), (b), (b'), (c) and (c) illustrate various types of the fluid-cartridges having yet another needle retraction mechanism in accordance with yet another embodiment of the present invention.

FIGS. 7(a) to 7(l) illustrate schematic details of operation of the fluid injecting system in accordance with an embodiment of the present invention.

FIGS. 8(a) to 8(i) illustrate schematic details of operation of the fluid injecting system in accordance with another embodiment of the present invention.

FIGS. 9(a) to 9(m) illustrate schematic details of operation of the fluid injecting system in accordance with yet another embodiment of the present invention.

Figure 10:
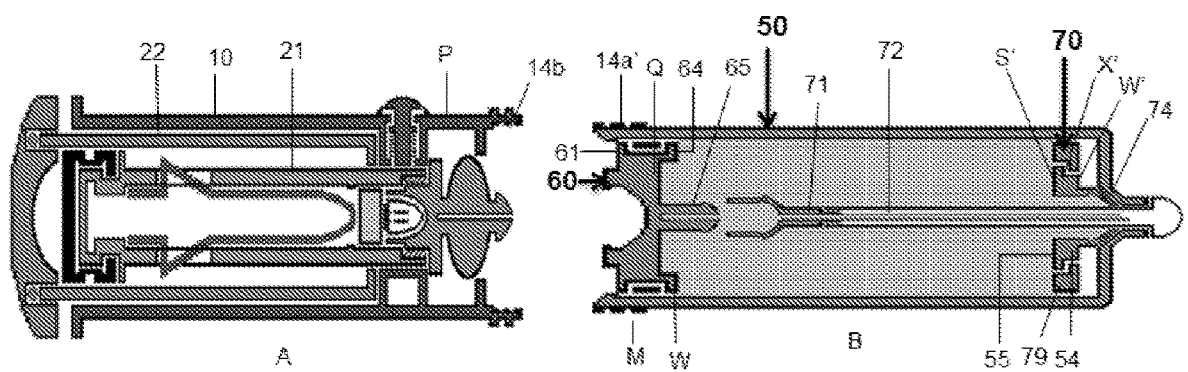

FIG. 10 illustrates schematic details of operation of the fluid injecting system in accordance with yet another embodiment of the present invention.

Figure 11:
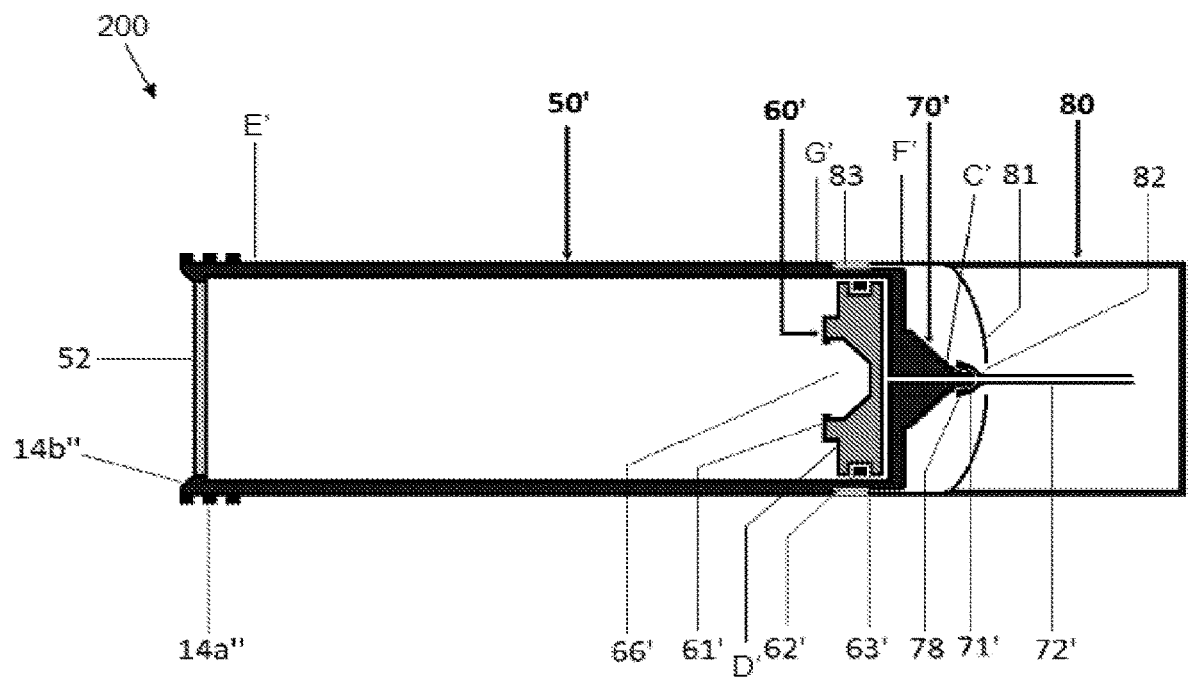

FIG. 11 illustrates a perspective view of a fluid collector in accordance with an embodiment of the present invention.

FIGS. 12(a) to 12(o) illustrate schematic details of operation of the fluid collector in accordance with an embodiment of the present invention.

Figure 13:
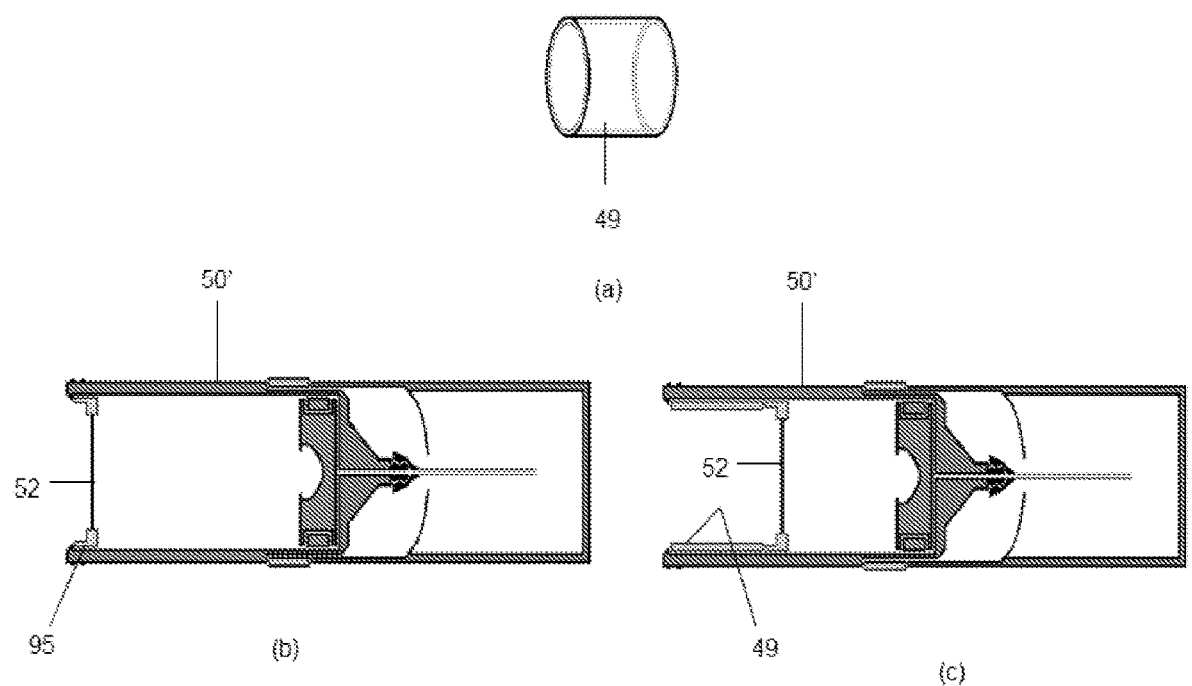

FIG. 13 illustrates (a) a hollow barrel ring; and (b), (c) insertion of the hollow barrel ring in the fluid collector in accordance with an embodiment of the present invention.

Figure 14:
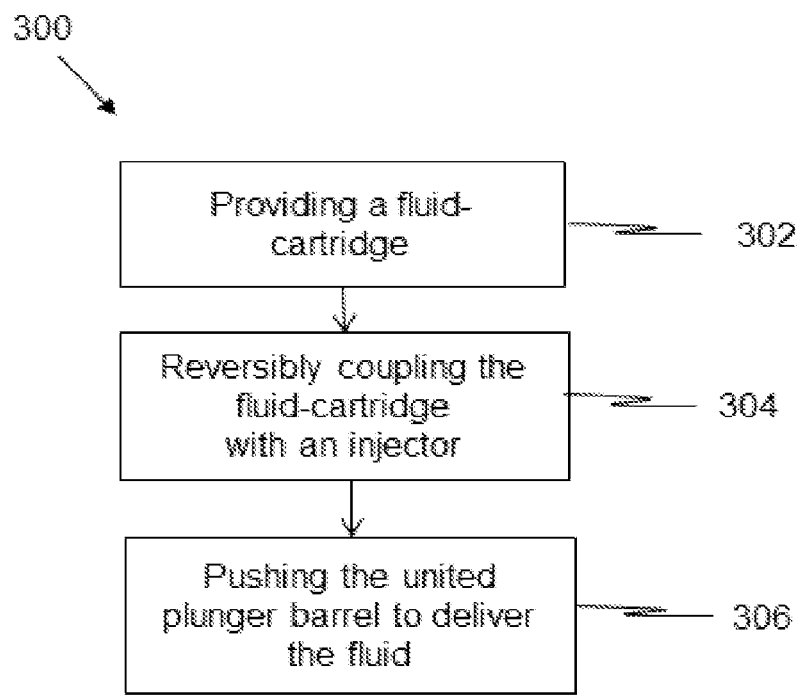

FIG. 14 is a flow chart illustrating fluid injecting method in accordance with an embodiment of the present invention.

Figure 15:
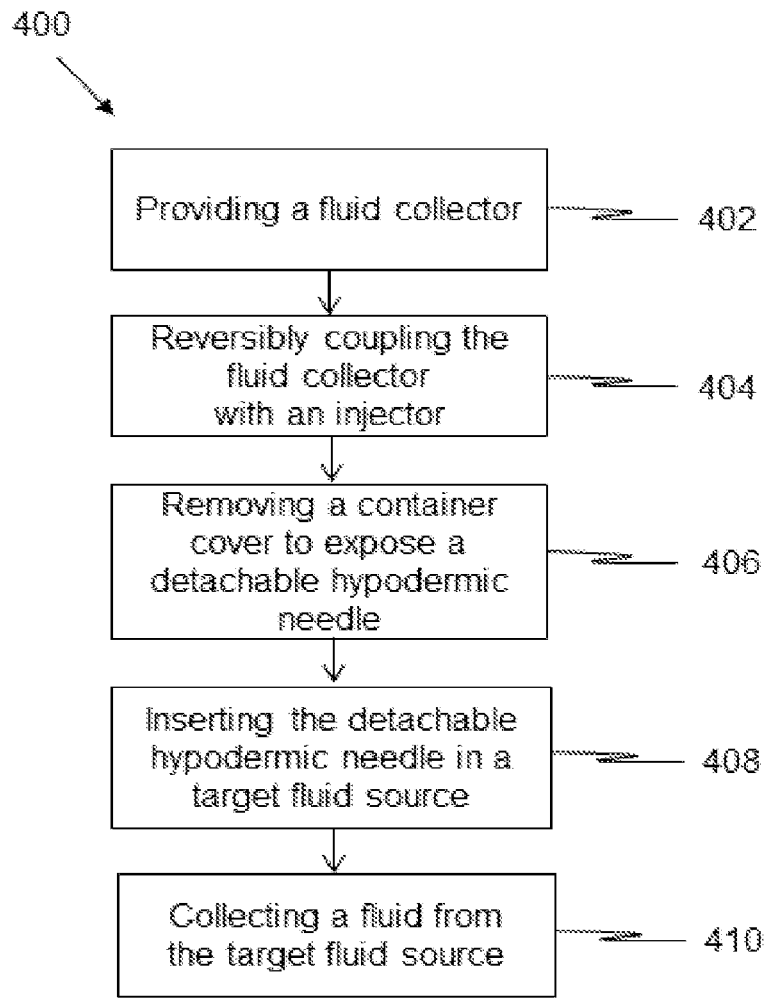

FIG. 15 is a flow chart illustrating a fluid collecting method in accordance with an embodiment of the present invention.

DETAILED DESCRIPTION OF THE ACCOMPANYING DRAWINGS

While the present invention is described herein by way of example using embodiments and illustrative drawings, those skilled in the art will recognize that the invention is not limited to the embodiments of drawing or drawings described, and are not intended to represent the scale of the various components. Further, some components that may form a part of the invention may not be illustrated in certain figures for ease of illustration, and such omissions do not limit the embodiments outlined in any way. It should be understood that the drawings and detailed description thereto are not intended to limit the invention to the particular form disclosed, but on the contrary, the invention is to cover all modifications, equivalents and alternatives falling within the scope of the present invention as defined by the appended claim. As used throughout this description, the word "may" is used in a permissive sense (i.e. meaning having the potential to), rather than the mandatory sense (i.e. meaning must). Further, the words "a" or "an" mean "at least one" and the word "plurality" means "one or more" unless otherwise mentioned. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes. Any discussion of documents, acts, materials, devices, articles and the like is included in the specification solely for the purpose of providing a context for the present invention. It is not suggested or represented that any or all of these matters form part of the prior art base or were common general knowledge in the field relevant to the present invention.

In this disclosure, whenever a composition or an element or a group of elements is preceded with the transitional phrase "comprising", it is understood that we also contemplate the same composition, element or group of elements with transitional phrases "consisting of", "consisting", "selected from the group of consisting of, "including", or "is" preceding the recitation of the composition, element or group of elements and vice versa.

The present invention is described hereinafter by various embodiments with reference to the accompanying drawing, wherein reference numerals used in the accompanying drawing correspond to the like elements throughout the description. This invention may, however, be embodied in many different forms and should not be construed as limited to the embodiment set forth herein. Rather, the embodiment is provided so that this disclosure will be thorough and complete and will fully convey the scope of the invention to those skilled in the art. In the following detailed description, numeric values and ranges are provided for various aspects of the implementations described. These values and ranges are to be treated as examples only, and are not intended to limit the scope of the claims. In addition, number of materials are identified as suitable for various facets of the implementations. These materials are to be treated as exemplary, and are not intended to limit the scope of the invention.

Figure 1:
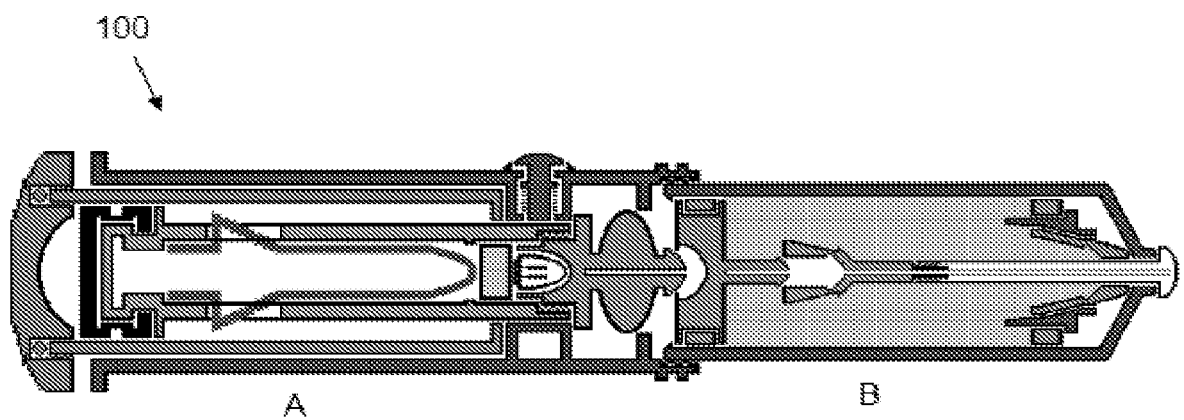
FIG. 1 illustrates a perspective view of a fluid injecting system in accordance with an embodiment of the present invention.

Referring to the drawings, the invention will now be described in more detail. In accordance with an embodiment of the present invention, the fluid injecting system (100), as showed in FIG. 1, comprising an injector (A) and a fluid-cartridge (B).

Figure 2:
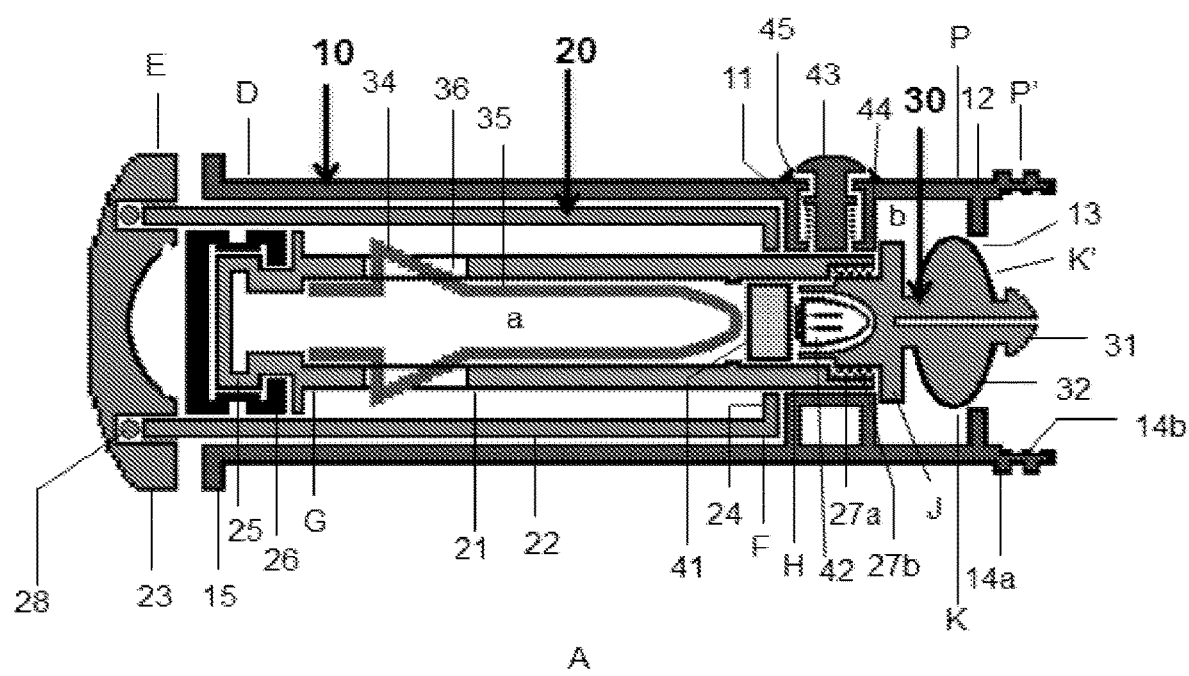
FIG. 2 illustrates a perspective view of an injector of the fluid injecting system in accordance with an embodiment of the present invention.

In accordance with an embodiment of the present invention, the injector (A), as shown in FIG. 2, comprises an injector body (10), a plunger assembly (20) and a plunger shaft (30). Further, the injector body (10) is a uniformly hollow, regular cylindrical body, which opens at both ends. The injector body (10) is having a partition ring (11) and a flange ring (12) at a proximal end (P') of the injector body (10) to hold the plunger shaft (30) in center of the injector body (10).

In accordance with an embodiment of the present invention, the injector body (10) further comprises of a finger flange (15) at a distal end (D) of the injector body (10) for holding the injector (A) and an inner engagement means (14 b) and an outer engagement means (14 a) at the proximal end (P') of the injector body (10) to firmly hold the fluid-cartridge (B) during an injection process. The inner engagement means (14 b) and the outer engagement means (14 a) are L-shaped grooves provided at both interior and exterior of the injector body (10) to firmly hold the fluid-cartridge (B) of smaller diameter and the fluid-cartridge (B) of larger diameter, respectively.

In accordance with an embodiment of the present invention, the plunger assembly (20) is having an inner plunger barrel (21) and an outer plunger barrel (22). Further, the inner plunger barrel (21) is slidable within the outer plunger barrel (22).

In accordance with an embodiment of the present invention, the outer plunger barrel (22) comprises of a uniformly regular and hollow cylindrical body having a thumb-rest (23) at a distal end (E) and an interiorly protruded flange rim (24) at a proximal end (F) of the outer plunger barrel (22). The thumb-rest (23) is configured to firmly hold a rubber O-ring (28). Further, an inner diameter of the interiorly protruded flange rim (24) is equal to the outer diameter of the inner plunger barrel (21). The outer plunger barrel (22) is having an outer diameter equal to inner diameter of the injector body (10) to facilitate smooth slidable axial movement of the outer plunger barrel (22) inside the injector body (10).

In accordance with an embodiment of the present invention, the inner plunger barrel (21) comprises of a uniformly regular and hollow cylindrical body having a piston seal holder (25) at a distal end (G) of the inner plunger barrel (21) to firmly hold a piston seal (26) between exterior of the inner plunger barrel (21) and interior of the outer plunger barrel (22). The inner plunger barrel (21) opens at a proximal end (H) and is configured to have a plurality of engagement means (27 a) to firmly hold a distal end (J) of the plunger shaft (30) by way of a plurality of engagement means (27 b).

In accordance with an embodiment of the present invention, the inner plunger barrel (21) comprises locking means. Further, the locking means is a U-clip locking means (35)

which is disposed inside the inner plunger barrel (21). The U-clip locking means (35) contains a conical lock-notch (34) at the distal end (G), which protrudes out passing through a longitudinal slot place (36) provided at the distal end (G) of the inner plunger barrel (21).

In accordance with an embodiment of the present invention, the outer plunger barrel (22) is configured for reversible engagement with locking means of the inner plunger barrel (21) to restrict movement of the outer plunger barrel (22) in forward direction facilitating the outer plunger barrel (22) and the inner plunger barrel (21) to unite forming a united plunger barrel (40), when the outer plunger barrel (22) is pulled out at its full length. Further, a vacuum (V) is generated between the outer plunger barrel (22) and the inner plunger barrel (21) upon formation of the united plunger barrel (40), as shown in FIG. 7(e).

In other words, the interiorly protruded flange rim (24) of the outer plunger barrel (22) passes over the conical lock-notch (34), when the outer plunger barrel (22) is pulled out in a backward direction. While passing over the conical lock-notch (34) of the U-clip locking means (35), the interiorly protruded flange rim (24) presses the conical lock-notch (34) inwardly to allow the flange rim (24) to slidably pass over the conical lock-notch (34) and move in backward direction, thereafter, the conical lock-notch (34) opens and retains its original state which restricts the movement of the outer plunger barrel (22) in forward direction. Thus, the U-clip locking means (35) facilitates the outer plunger barrel (22) and the inner plunger barrel (21) to unite to form the united plunger barrel (40).

In accordance with an embodiment of the present invention, the plunger shaft (30) is a straight rod like structure of desirable length and is provided with the plurality of engagement means (27 b) at the distal end (J) to firmly attach with the inner plunger barrel (21). The plunger shaft (30) is configured to have an axially furrowed forceps-lock head (31) containing two outwardly protruded flaps (32) at a proximal end (K) on both sides of the furrowed forceps-lock head (31). The flaps (32) are configured to be sharp-edged blades at a proximal end (K') of the flaps (32). Further, the flaps (32) slidably pass through a central passage (13) of the flange ring (12) with axial movement of the plunger shaft (30) in forward and backward directions along with respective movement of the inner plunger barrel (21).

In accordance with an embodiment of the present invention, the plunger assembly (20) is housed inside a distal chamber (a) of the injector (A) and the plunger shaft (30), axially attached at the proximal end (H) of the inner plunger barrel (21) is housed axially at center of a proximal chamber (b) of the injector (A). The forceps-lock head (31) of the plunger shaft (30) passes through the flange ring (12) through the central passage (13) and the forceps-lock head (31) remains initially in closed position due to pressed flaps (32) when held within the central passage (13) of the flange ring (12).

In accordance with an embodiment of the present invention, the plunger assembly (20) is configured to have a first spring. Further, the first spring is provided between exterior of the inner plunger barrel (21) and interior of the outer plunger barrel (22) of the plunger assembly (20).

In accordance with an embodiment of the present invention, the proximal end (H) of the inner plunger barrel (21) is provided with plurality of button cells (41) and a LED indicator (42) enabling an injectable site to be visible by way of tyndall effect on a fluid (53) facilitating the injection process in dark too. An outer surface of the inner plunger barrel (21) is provided with a plurality of intrusions to hold a plurality of metallic strips to form a LED circuit. The LED indicator (42) is configured to switch on as soon as the outer plunger barrel (22) is pulled in the backward direction and the vacuum (V) is created in the united plunger barrel (40). Further, the LED indicator (42) is configured to switch off on completion of the injection process, as and when the vacuum (V) is released and the outer plunger barrel (22) as well as the inner plunger barrel (21) retain their initial states. Further, the injector (A) is having a push-button (43) placed on a septum (44) at a proximal end (P) of the injector (A). Preferably, the push-button (43) is provided with a second spring (45). The push-button (43) may be used, if required, to restrict and conveniently control the backward movement of the united plunger barrel (40) during a fluid collection process by pressing the push-button (43).

Figure 3:
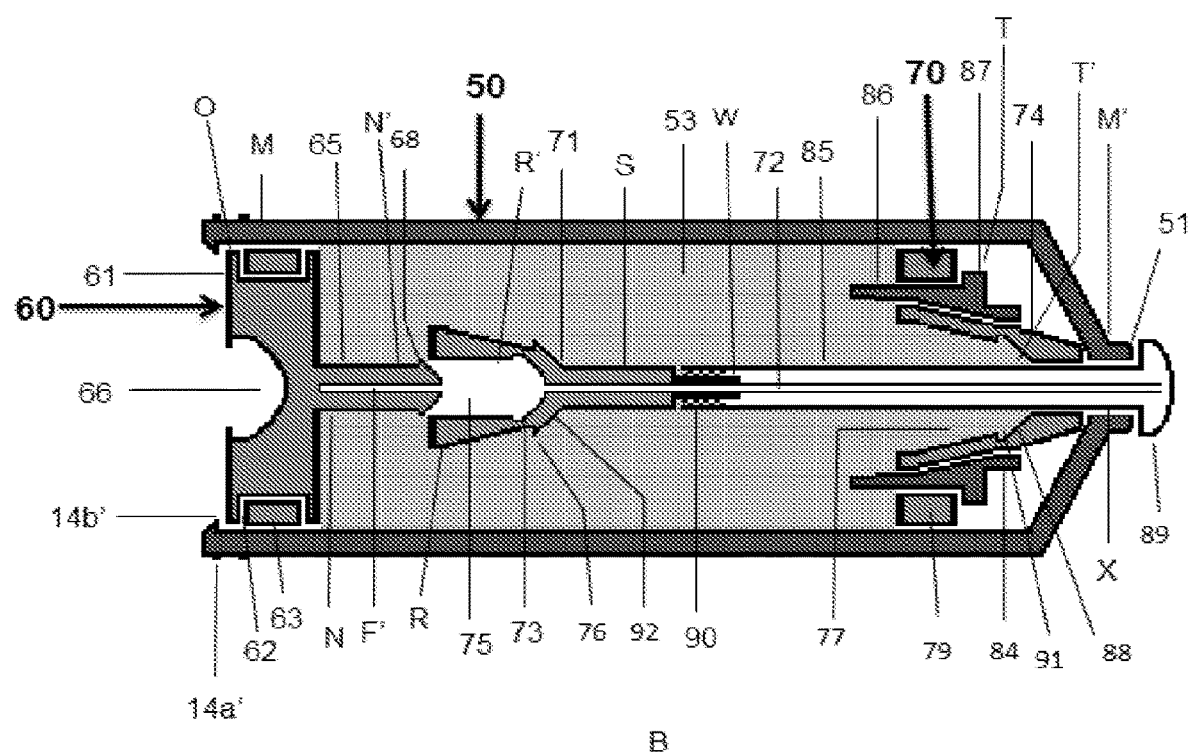
FIG. 3 illustrates a perspective view of a fluid-cartridge of the fluid injecting system in accordance with an embodiment of the present invention.
Figure 3A:
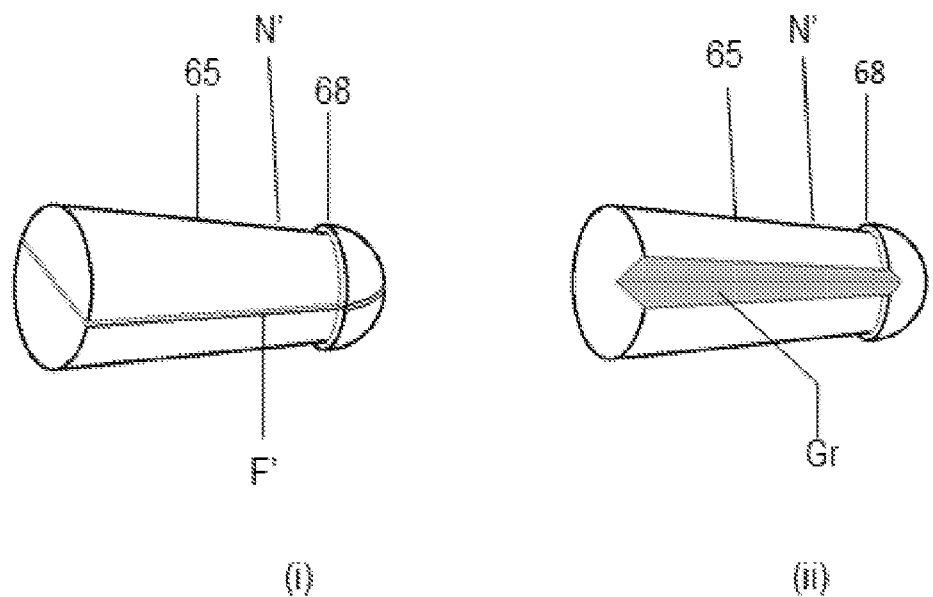
FIG. 3(a) illustrates various needle catch projections of the fluid-cartridge in accordance with an embodiment of the present invention.

In accordance with an embodiment of the present invention, the fluid-cartridge (B), as shown in FIG. 3, comprises the fluid (53) and a hypodermic needle (72) for injecting the fluid (53) at the injectable site. The fluid-cartridge (B) may be releasably engaged with the injector (A) at the proximal end (P) of the injector (A). Further, the fluid-cartridge (B) is having a constant length. Also, the fluid (53) is an injectable fluid.

In accordance with an embodiment of the present invention, the fluid-cartridge (B) further comprises a fluid container (50), a piston assembly (60) and a retractable needle assembly (70).

In accordance with an embodiment of the present invention, the fluid container (50) is a uniformly regular and hollow cylindrical body opening at both distal end (M) and proximal end (M') and is configured to contain the fluid (53). The fluid container (50) is having engagement means (14 a', 14 b') at the distal end (M) of the fluid container (50) to firmly engage within the L-shaped grooves of the inner engagement means (14 b) and the outer engagement means (14 a) of the injector body (10). Further, the engagement means (14 a', 14 b') are protrusions provided at both interior and exterior of the fluid container (50).

In accordance with an embodiment of the present invention, the piston assembly (60) comprises a piston flange (61) and a conical cavity (66) to receive and retain the forceps-lock head (31) during the injection process. The piston flange (61) is configured to have a needle catch projection (65) at center of the piston assembly (60) at a proximal end (N) of the piston assembly (60).

The needle catch projection (65) may be provided with a longitudinal furrow (F') or a conical groove (Gr) at surface as shown in FIGS. 3 (a) (i) and 3 (a) (ii). The needle catch projection (65) is also provided with a conical ridge (68) at a proximal end (N') of the needle catch projection (65). Further, rim of the piston flange (61) is configured to have plurality of grooves (62) to hold a piston seal (63) between the piston flange (61) and the fluid container (50).

In accordance with an embodiment of the present invention, the conical cavity (66) is positioned at center of the piston assembly (60) at a distal end (0) of the piston assembly (60) to receive and retain the forceps-lock head (31) during the injection process. The conical cavity (66) is having an opening diameter greater than an outer diameter of closed forceps-lock head (31) of the plunger shaft (30) to receive the closed forceps-lock head (31) conveniently, whereas, the opening diameter of the conical cavity (66) is lesser than the inner diameter of the conical cavity (66) to firmly engage with opened forceps-lock head (31) of the plunger shaft (30).

In accordance with an embodiment of the present invention, the retractable needle assembly (70) comprises a needle hub (71) configured to hold the hypodermic needle (72), a needle holder (74) configured to hold the needle hub (71), an O-ring (79), a cap (84) having a plurality of horizontally extended pins (86) towards the distal end (M) of the fluid container (50) and a needle guard (85) configured to cover the hypodermic needle (72) disposed inside the fluid container (50). Further, the hypodermic needle (72) is uniformly hollow regular and straight, and of desired dimensions. Furthermore, the retractable needle assembly (70) may be provided without the hypodermic needle (72).

In accordance with an embodiment of the present invention, the needle hub (71) comprises of a conical cavity (75) at a distal end (R) of the needle hub (71). The conical cavity (75) is configured to have a conical groove (73) at a proximal end (R') of the conical cavity (75) which is slightly greater in diameter than the conical ridge (68) of the needle catch projection (65) of the piston flange (61) to conveniently receive and fixedly engage with the needle catch projection (65). An outer diameter of the needle hub (71) at the distal end (R) is comparatively greater than a proximal end (S) of the needle hub (71) to constitute a cone shaped structure, which is provided with a conical ridge (76) at the proximal end (S) of the needle hub (71) to fixedly attach within a conical groove (91) of a conical cavity (77) of the needle holder (74) at a proximal end (T') of the needle holder (74). Further, the needle hub (71) holds the hypodermic needle (72) at center position at a proximal end (S) of the needle hub (71). The hypodermic needle (72) is encapsulated inside the needle guard (85) with the help of a locking means (90). The needle guard (85) may be removed from the needle hub (71) to expose the hypodermic needle (72) by drawing out and thereafter, rotating the needle guard (85) in an anti-clockwise direction at 90-degree angle with the help of a knob like structure (89) provided at a proximal end (X) of the needle guard (85). The proximal end (M') of the fluid container (50) is provided with a centrally opened conical mouth (51) to hold the retractable needle assembly (70). Further, the needle guard (85) may be provided without the knob like structure (89).

In accordance with an embodiment of the present invention, an inner diameter of the conical cavity (75) of the needle hub (71) is equal to an outer diameter of the needle catch projection (65) of the piston flange (61) to receive and firmly engage with the needle catch projection (65).

In accordance with an embodiment of the present invention, an inner diameter of the conical cavity (77) of the needle holder (74) is equal to an outer diameter of the needle hub (71) to receive and firmly engage with the needle hub (71). Further, the inner diameter of a conical cavity of the cap (84) is equal to the outer diameter of the needle holder (74) to receive and firmly engage with the needle holder (74). Furthermore, the needle holder (74) and the needle hub (71) may be fused together.

In accordance with an embodiment of the present invention, the plurality of horizontally extended pins (86) of the cap (84) are configured to pass through a plurality of clefts of the O-ring (79) to slidably hold the O-ring (79). The cap (84) is provided with a flange (87) at a proximal end (T) of the cap (84) and the conical cavity of the cap (84) is configured to hold the needle holder (74). Further, the needle holder (74) and the cap (84) are provided at the proximal end (M') of the fluid container (50).

In accordance with an embodiment of the present invention, the needle holder (74) has an outer diameter equal to an inner diameter of the O-ring (79) as well as an inner diameter of the cap (84). Further, an inner surface of the conical cavity (77) of the needle holder (74) at a proximal end (T') is provided with uniform fine groove linings (88) which are uniformly similar and equal in numbers to fixedly hold and accommodate all the groove linings (92) provided at the proximal end (S) of an outer surface of the needle hub (71) to prevent rotation of the needle hub (71), while rotating the needle guard (85) in the anti-clockwise direction in order to remove the needle guard (85) to expose the hypodermic needle (72) before the injection process.

In accordance with an embodiment of the present invention, the O-ring (79) has an outer diameter equal to an inner diameter of the fluid container (50), whereas the inner diameter of the O-ring (79) is equal to the outer diameter of the needle holder (74). The O-ring (79) is provided with the plurality of clefts, exactly equal in shape and number of the horizontally extended pins (86) of the cap (84). The plurality of clefts of the O-ring (79) is configured to slidably engage with the horizontally extended pins (86) of the cap (84).

In accordance with an embodiment of the present invention, the needle guard (85) is drawn out by a user with the help of the knob like structure (89) allowing the hypodermic needle (72) along with the needle guard (85) to extend out of the needle holder (74). Further, the needle guard (85) is having an outer diameter equal to the opened conical mouth (51) of the fluid container (50).

In other words, when the needle guard (85) is drawn out by the user using the knob like structure (89), the needle hub (71) becomes fixedly engage within the conical cavity (77) of the needle holder (74) and the groove linings (88) provided in the conical cavity (77) of the needle holder (74) fixedly engage and accommodate all the groove linings (92) provided at the proximal end (S) of the needle hub (71). The needle guard (85) may be removed by rotating in the anti-clockwise direction at the 90-degree angle, which unlocks the locking means (90) and thereafter, the needle guard (85) is separated from the needle hub (71) to expose the hypodermic needle (72).

In accordance with an embodiment of the present invention, the united plunger barrel (40) of the injector (A) is pushed through the thumb-rest (23) in forward direction to firmly attach the forceps-lock head (31) of the plunger shaft (30) within the conical cavity (66) of the piston assembly (60) forming a single plunger unit (67) as shown in FIG. 7(*f*). On pushing a proximal end (69) of the single plunger unit (67) in forward direction, the piston assembly (60) pushes the fluid (53) in forward direction, which is injected at the injectable site through the hypodermic needle (72). At the end point of the injection process, the proximal end (N) of the piston assembly (60) comes in close contact of the plurality of horizontally extended pins (86) and the needle catch projection (65) gently begins entering into the conical cavity (75) of the needle hub (71). Exerting further pressure by the piston assembly (60) on the plurality of horizontally extended pins (86) of the cap (84) results in sliding of the plurality of horizontally extended pins (86) in forward direction to set the needle holder (74) free in order to release the needle holder (74) holding the needle hub (71) along with the hypodermic needle (72).

Figure 4:
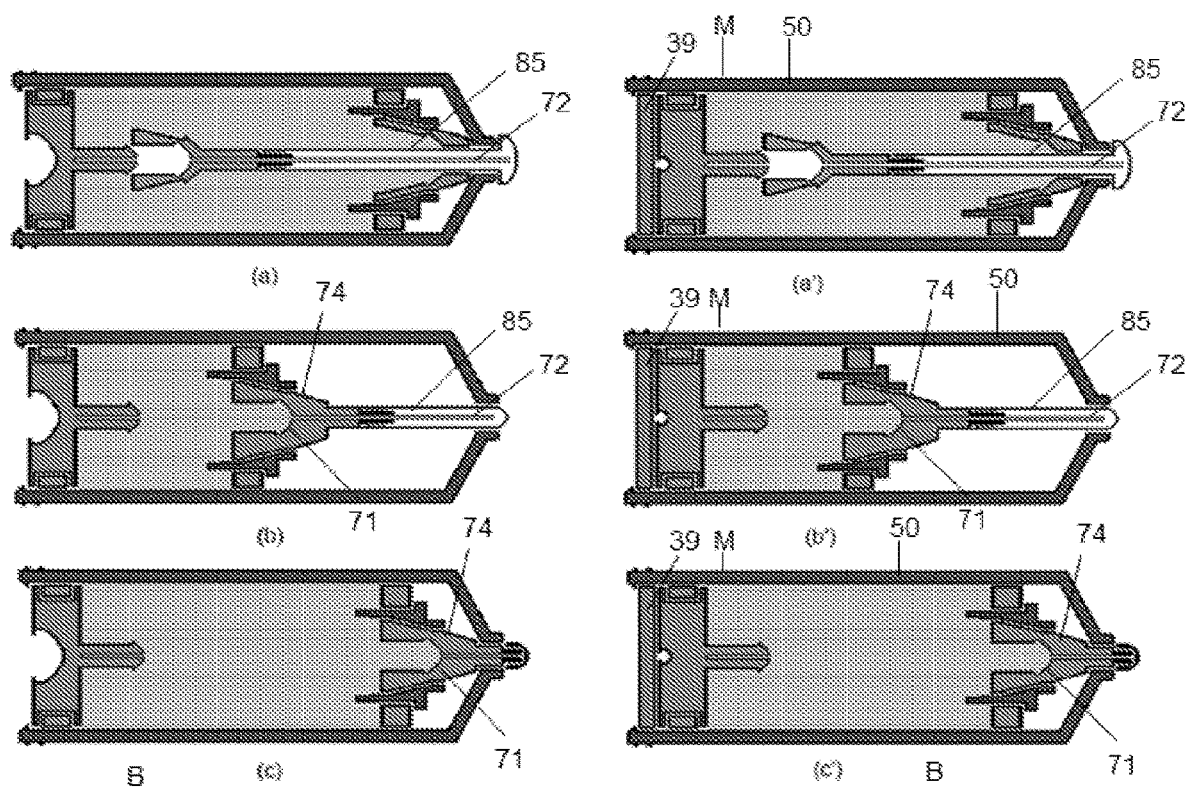

FIG. 4(*a*), (*a'*), (*b*), (*b'*), (*c*) and (*c'*) illustrate various types of the fluid-cartridges (B) having a needle retraction mechanism in accordance with an embodiment of the present invention.

In accordance with an embodiment of the present invention, the fluid-cartridges (B), as shown in FIGS. 4(*a*) and (*a'*) are provided with the hypodermic needle (72) wherein the hypodermic needle (72) is required to be pulled out manually and thereafter, removing the needle guard (85). The fluid-cartridge (B) may be provided with the hypodermic needle (72) as shown in FIGS. 4 (b) and (b'), wherein the hypodermic needle (72) comes out along with the needle guard (85) due to pressure exerted on the united plunger barrel (40). Further, the needle holder (74) and the needle hub (71) of these fluid-cartridges (B) are fused together. Furthermore, the fluid-cartridges (B) may be provided without the hypodermic needle (72) as shown in FIGS. 4(c) and (c'), wherein the user may attach the desired hypodermic needle (72) of desired length or bore. The needle holder (74) and the needle hub (71) of these fluid-cartridges (B) are also fused together.

As shown in FIGS. 4 (a), (b) and (c), the fluid-cartridges (B) are releasably coupled with the injector (A) having the plunger shaft (30) with the axially furrowed forceps-lock head (31). In other embodiments, as shown in FIGS. 4 (a'), (b') and (c'), the fluid containers (50) of the fluid-cartridges (B) are configured to have a rubber cap (39) at the distal end (M) of the fluid container (50). Further, these fluid-cartridges (B) are releasably coupled with the injector (A) having a needle shaped plunger shaft (38).

Figure 5:
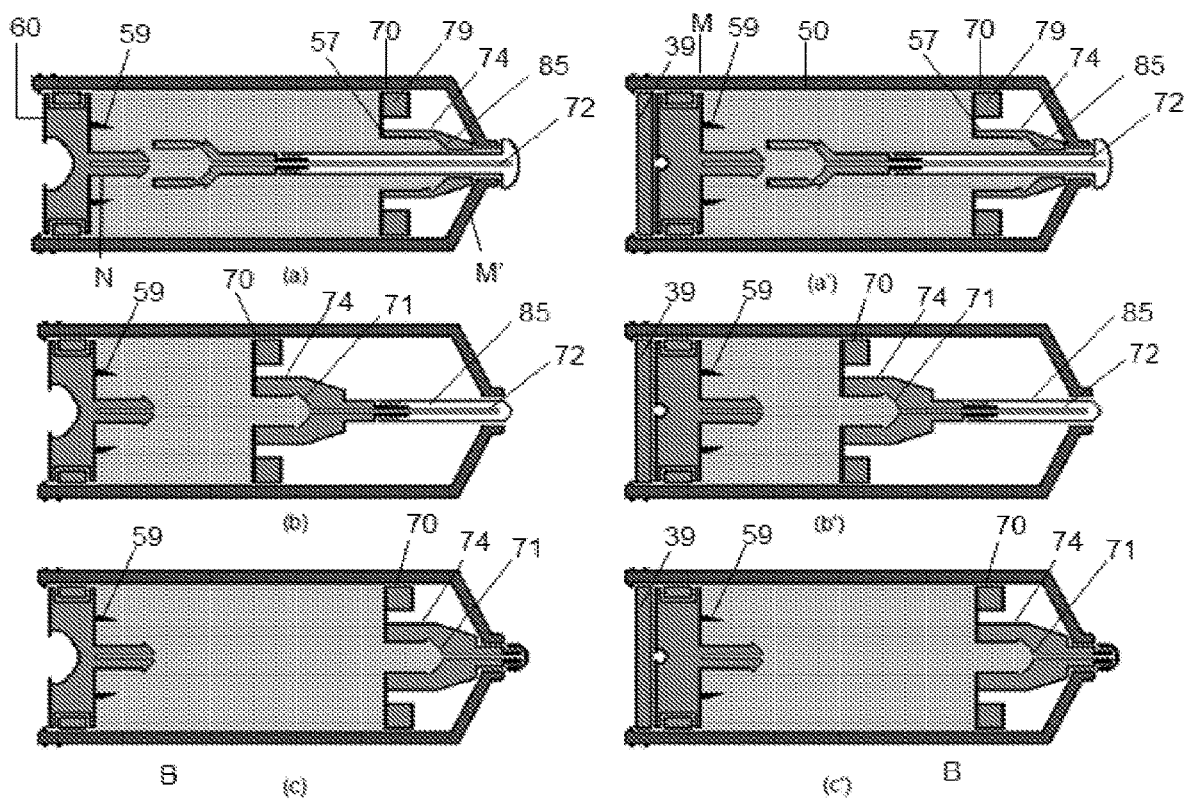

FIGS. 5 (a), (a'), (b), (b'), (c) and (c') illustrate various types of the fluid-cartridges (B) having different needle retraction mechanism in accordance with another embodiment of the present invention.

As shown in FIGS. 5 (a), (a'), (b), (b'), (c) and (c'), the fluid-cartridges (B) are configured to have a cylindrical saw blade (59) at the proximal end (N) of the piston assembly (60) of the fluid-cartridges (B). These fluid-cartridges (B) are provided with the retractable needle assembly (70) comprising a circular O-ring (79) having the needle holder (74) at center at the proximal end (M') of the fluid container (50). Further, the circular O-ring (79) is provided with a thin layer circular diaphragm (57) between the circular O-ring (79) and the needle holder (74).

The fluid-cartridges (B), as shown in FIGS. 5(a) and (a') are provided with the hypodermic needle (72) wherein the hypodermic needle (72) is required to be pulled out manually and thereafter, removing the needle guard (85), In the fluid cartridges (B) as shown in FIGS. 5 (b) and (b'), the needle hub (71) and the needle holder (74) are fused together to constitute the retractable needle assembly (70) as a single unit which is further provided with the hypodermic needle (72) along with the needle guard (85). Further, the hypodermic needle (72) along with the needle guard (85) comes out of the fluid-cartridges (B) due to the pressure exerted on the united plunger barrel (40). Furthermore, the fluid-cartridges (B) may be provided without the hypodermic needle (72) as shown in FIGS. 5(c) and (c'), wherein the user may attach the desired hypodermic needle (72) of the desired length or bore. The needle holder (74) and the needle hub (71) of these fluid-cartridges (B) are also fused together to constitute the retractable needle assembly (70) as a single unit.

In accordance with an embodiment of the present invention, the fluid-cartridges (B), as shown in FIGS. 5 (a), (b) and (c), are releasably coupled with the injector (A) having the plunger shaft (30) with the axially furrowed forceps-lock head (31). As shown in FIG. 5 (a'), (b') and (c'), the fluid containers (50) of the fluid-cartridges (B) are configured to have the rubber cap (39) at the distal end (M) of the fluid container (50). Further, these fluid-cartridges (B) are releasably coupled with the injector (A) having the needle shaped plunger shaft (38).

Figure 6:
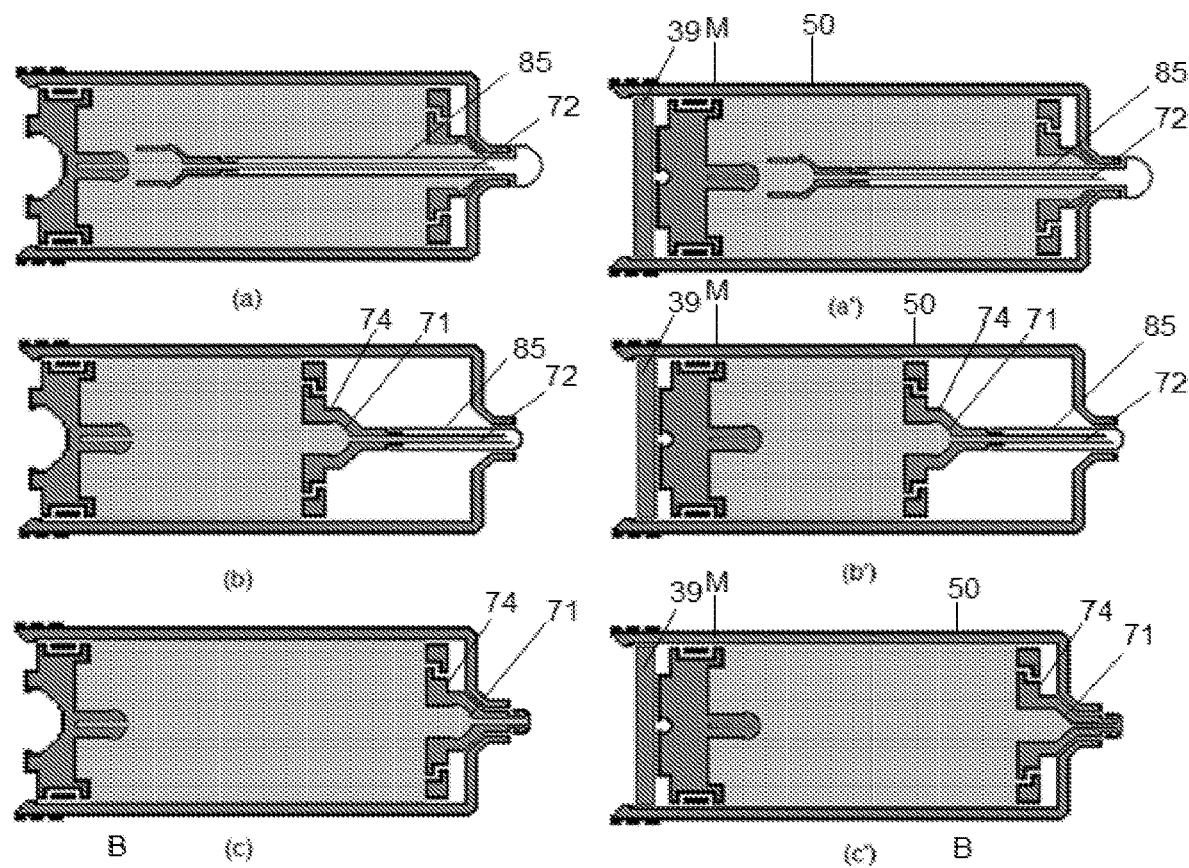

FIGS. 6 (a), (a'), (b), (b'), (c) and (c') illustrates various types of the fluid-cartridges (B) having different needle retraction mechanism in accordance with yet another embodiment of the present invention.

As shown in FIGS. 6 (a) and (a'), the fluid-cartridges (B) are provided with the hypodermic needle (72) wherein the hypodermic needle (72) is required to be pulled out manually and thereafter, removing the needle guard (85). The fluid-cartridge (B) may be provided with the hypodermic needle (72) as shown in FIGS. 6 (b) and (b'), wherein the hypodermic needle (72) comes out along with the needle guard (85) due to pressure exerted on the united plunger barrel (40). Further, the needle holder (74) and the needle hub (71) of these fluid-cartridges (B) are fused together. Furthermore, the fluid-cartridges (B) may be provided without the hypodermic needle (72) as shown in FIGS. 6 (c) and (c'), wherein the user may attach the desired hypodermic needle (72) of the desired length or bore. The needle holder (74) and the needle hub (71) of these fluid-cartridges (B) are also fused together.

In accordance with an embodiment of the present invention, the fluid-cartridges (B), as shown in FIGS. 6 (a), (b) and (c), are releasably coupled with the injector (A) having the plunger shaft (30) with the axially furrowed forceps-lock head (31). As shown in FIGS. 6 (a'), (b') and (c'), the fluid containers (50) of the fluid-cartridges (B) are configured to have the rubber cap (39) at the distal end (M) of the fluid container (50). Further, these fluid-cartridges (B) are releasably coupled with the injector (A) having the needle shaped plunger shaft (38). Furthermore, the different needle retraction mechanisms are elaborated in FIGS. below.

The schematic details of operation of the fluid injecting system (100) are shown in FIG. 7(a) to FIG. 7(l).

Figure 7A:
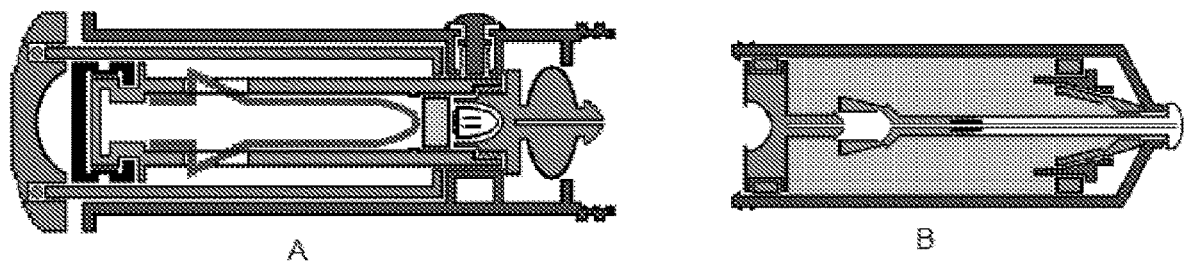
Figure 7B:
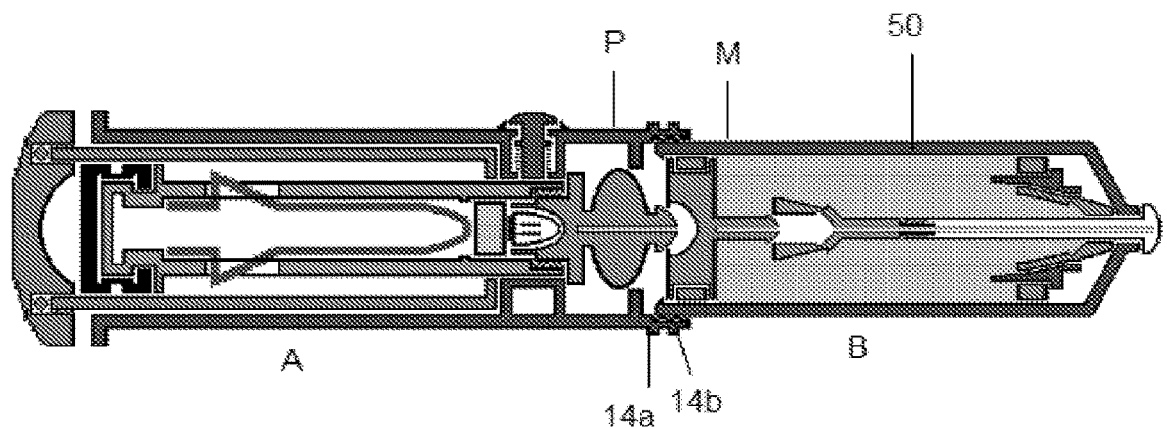

FIG. 7(a) illustrates the injector (A) and the fluid-cartridge (B) as shown in FIG. 4(a) of the fluid injecting system (100) in accordance with an embodiment of the present invention. Prior to the injection process, the distal end (M) of the fluid container (50) of the fluid-cartridge (B) is attached at the proximal end (P) of the injector (A) through the inner engagement means (14 b) and the outer engagement means (14 a) of the injector body (10) of the injector (A) to the engagement means (14 a', 14 b') of the fluid container (50) to constitute the fluid injecting system (100) as shown in FIG. 7(b).

Figure 7C:
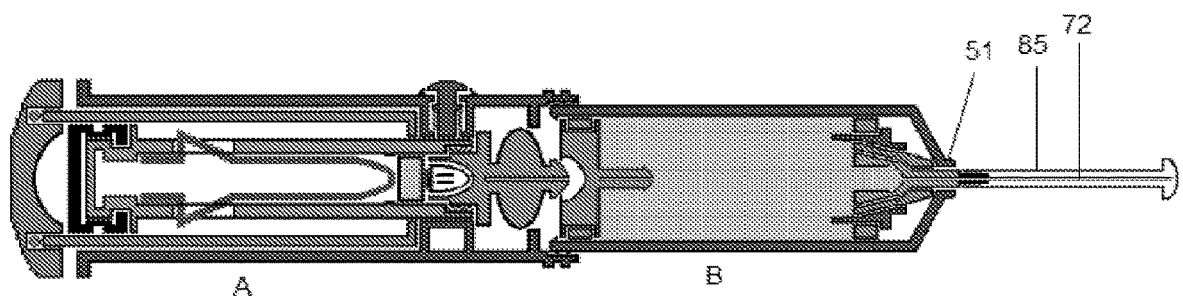
Figure 7D:
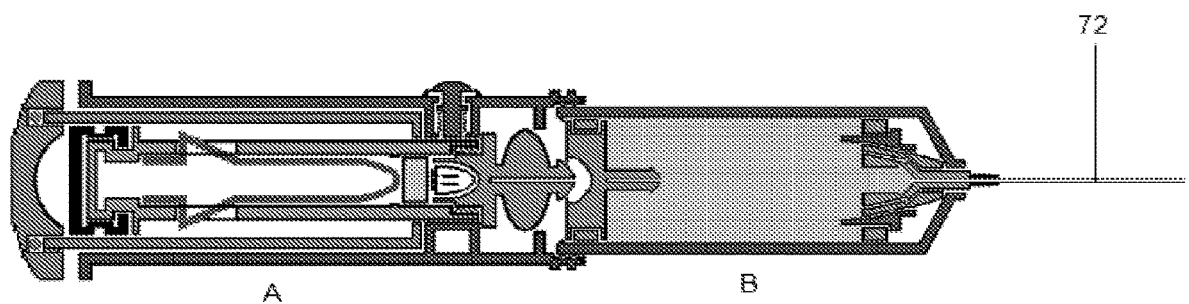
Figure 7E:
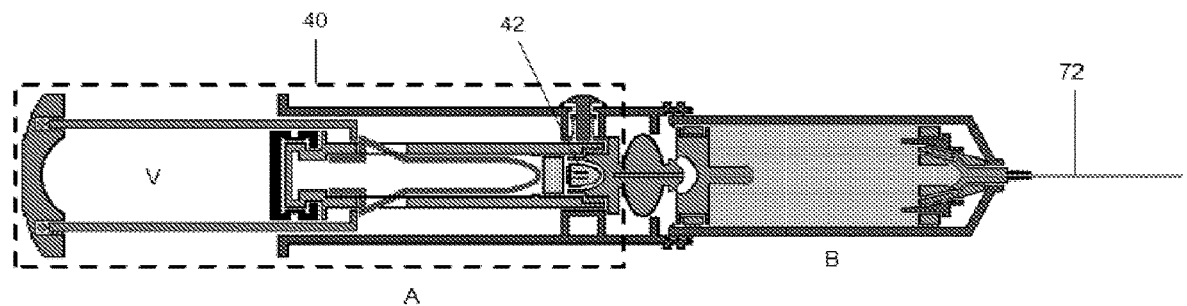

As shown in FIG. 7(c), the needle guard (85) along with the hypodermic needle (72) is drawn out by the user, which facilitates the hypodermic needle (72) along with the needle guard (85) to extend out through the opened conical mouth (51) of the fluid container (50) and the needle holder (74) click fits with the needle hub (71). Thereafter, the needle guard (85) is rotated in the anticlockwise direction by 90 degrees to unlock the locking means (90) and drawn to remove the needle guard (85) to expose the hypodermic needle (72) as shown in FIG. 7(d).

Figure 7F:
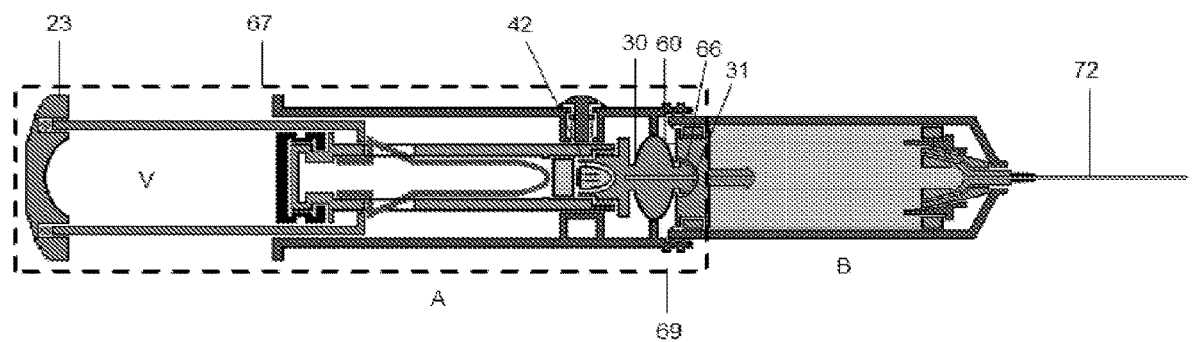
Figure 7G:
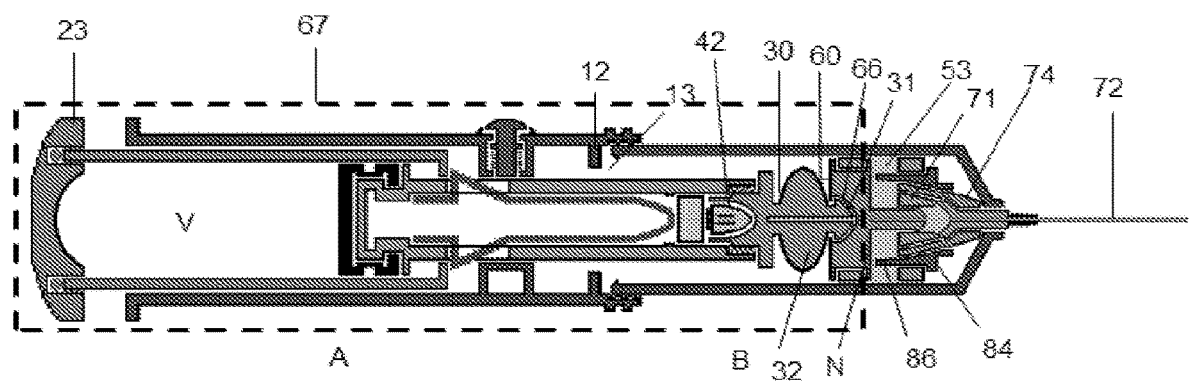

FIG. 7(e) illustrates the united plunger barrel (40) of the fluid injecting system (100) in accordance with an embodiment of the present invention. As shown in FIG. 7(e), the LED indicator (42) gets switched-on and glows as soon as the vacuum (V) is generated in the united plunger barrel (40) and illuminates the end tip of the hypodermic needle (72) and surrounding area of the injectable site to indicate ongoing injection process to guide the user and to facilitate injection process in dark too. On pushing the united plunger barrel (40) through the thumb-rest (23), the forceps-lock head (31) of the plunger shaft (30) gently enters into the conical cavity (66) of the piston assembly (60) and constitutes a single plunger unit (67) as shown in FIG. 7(f). As soon as the flaps (32) passthrough the central passage (13) of the flange ring (12), the forceps-lock head (31) opens and gets engage firmly with the piston assembly (60) occupying the inner space of the conical cavity (66). On further pushing the proximal end (69) of the single plunger unit (67), the piston assembly (60) simultaneously pushes the fluid (53) in forward direction, which is injected into the body through the hypodermic needle (72). Just before the completion of the injection process, the proximal end (N) of the piston assembly (60) comes in close contact of end tips of the plurality of horizontally extended pins (86) of the cap (84) holding the needle holder (74) and the needle hub (71), as shown in FIG. 7(g). On further pushing the single plunger unit (67) in forward direction, the plurality of horizontally extended pins (86) begin sliding in forward direction to dislodge the needle holder (74) from grip of the cap (84). At the same time, the needle catch projection (65) of the piston assembly (60) also gently enters into the conical cavity (75) of the needle hub (71) and gets engage therein to attach the retractable needle assembly (70) with the help of the conical ridge (76) occupying the conical groove (91) of the conical cavity (77) of the needle holder (74) as shown in FIG. 7(h).

Figure 7H:
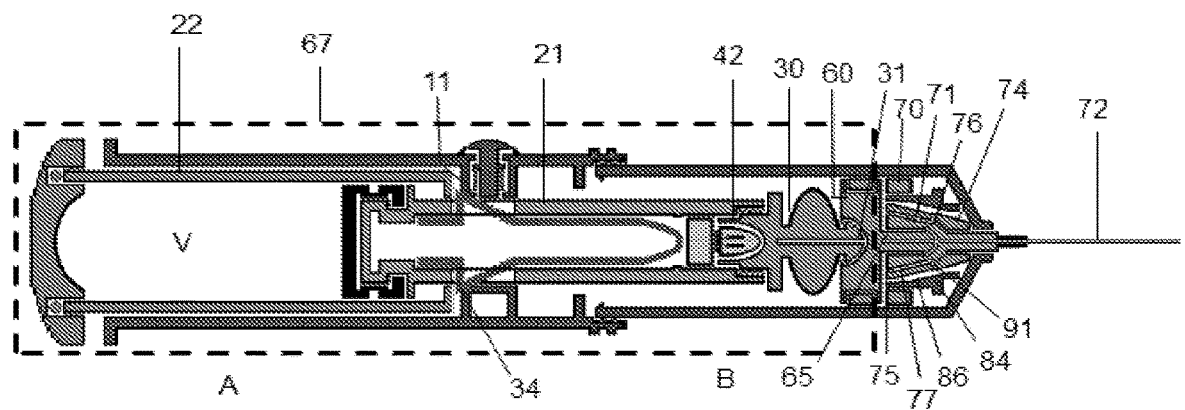
Figure 7I:
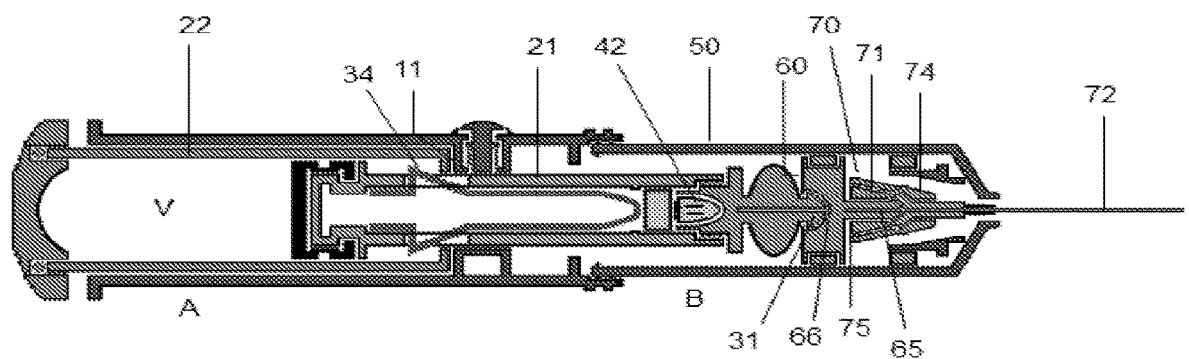

At the end of the injection process, as shown in FIG. 7(h), the plurality of horizontally extended pins (86) holding the needle hub (71) slide completely in forward direction to dislodge the needle hub (71) along with the needle holder (74) from the close contact of the cap (84). Simultaneously, the conical lock-notch (34) firmly engaging the outer plunger barrel (22) to the inner plunger barrel (21) itself presses inwardly, while axially passing through passage of the partition ring (11) in forward direction. It unlocks and releases the outer plunger barrel (22) and consequently, the inner plunger barrel (21) moves in backward direction due to reduced pressure of the vacuum (V) between the outer plunger barrel (22) and the inner plunger barrel (21). Since, the forceps-lock head (31) is firmly engaged within the conical cavity (66) of the piston assembly (60) and the piston assembly (60) itself is engaged with the retractable needle assembly (70) through engagement of the needle catch projection (65) with the conical cavity (75) of the needle hub (71), movement of the inner plunger barrel (21) in the backward direction gently retracts the hypodermic needle (72) along with the needle holder (74) holding the needle hub (71) due to the reduced pressure of the vacuum (V), as shown in FIG. 7(i).

Also, the first spring of the plunger assembly (20) may help in the backward movement of the inner plunger barrel (21) along with the hypodermic needle (72). The first spring is compressed when the outer plunger barrel (22) is pulled out at its full length to constitute the united plunger barrel (40) and the vacuum (V) is created between the inner plunger barrel (21) and the outer plunger barrel (22). As soon as the outer plunger barrel (22) is unlocked from the conical lock-notch (34) at the end of the injection process, compression of the first spring is gradually released which results in the backward movement of the inner plunger barrel (21) along with the hypodermic needle (72). Further, combination of both the vacuum (V) and the first spring may help in the backward movement of the inner plunger barrel (21) along with the hypodermic needle (72).

Figure 7J:
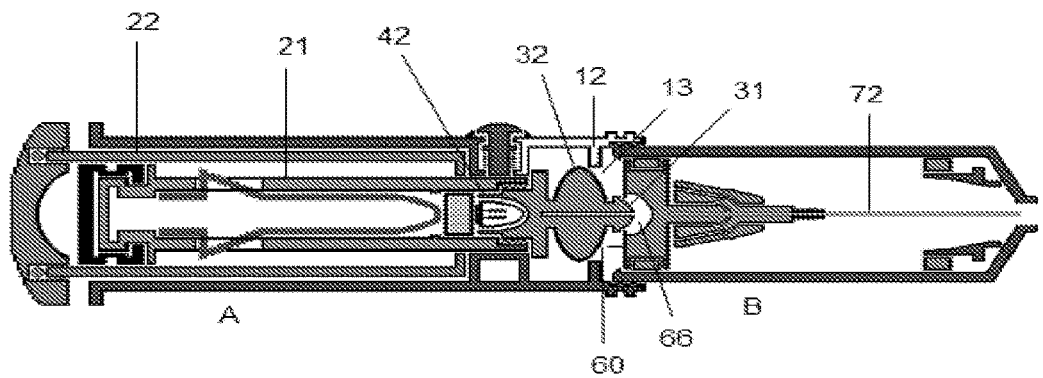

As shown in FIG. 7(j), during the movement of the inner plunger barrel (21) in the backward direction, the flaps (32) pass through the central passage (13) of the flange ring (12) and press inwardly resulting in closure of the forceps-lock head (31), releasing itself from the conical cavity (66) of the piston assembly (60), leaving behind the hypodermic needle (72) encapsulated within an empty fluid-cartridge (B). Thus, the inner plunger barrel (21) along with plunger shaft (30) attains its initial state soon after the vacuum (V) between the inner plunger barrel (21) and the outer plunger barrel (22) is completely released. As soon as the injection process completes, the LED indicator (42) gets switched off indicating the completion of the injection process.

Figure 7K:
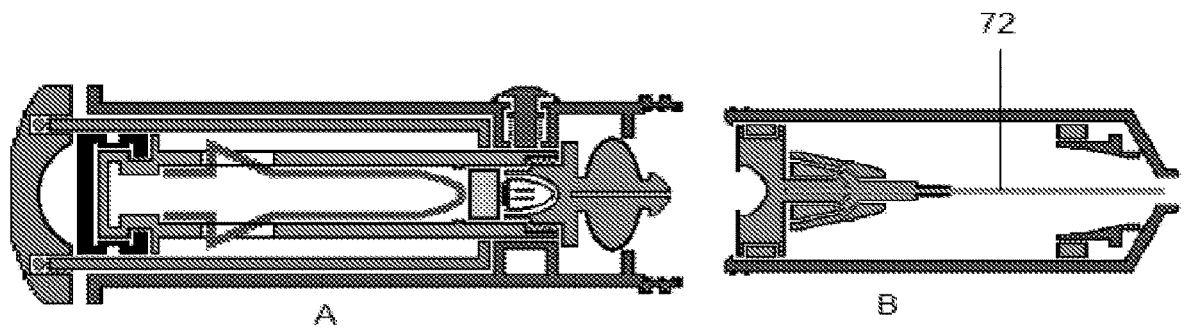
Figure 7L:
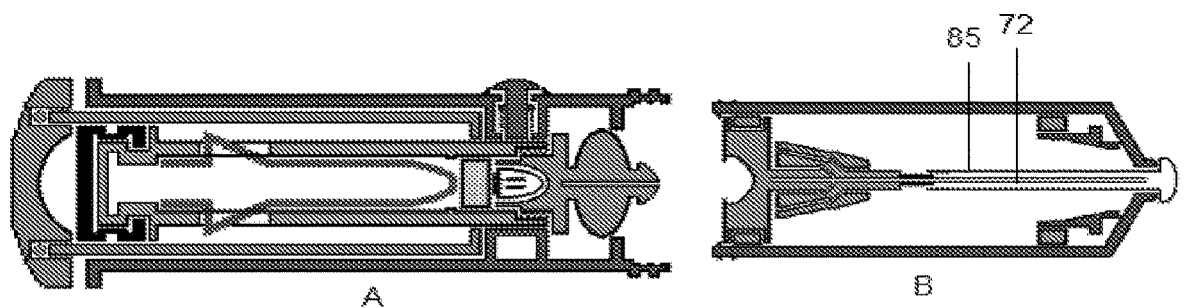

As shown in FIG. 7(k), the empty fluid-cartridge (B) encapsulating the hypodermic needle (72) is detached from the injector (A) to dispose of safely, whereas the injector (A) finally attains its original state to become ready for next operation. Further, the needle guard (85) may be inserted on the retracted hypodermic needle (72) in the empty fluid-cartridge (B) as shown in FIG. 7(l).

FIG. 8 (a) illustrates the injector (A) having the needle shaped plunger shaft (38) and the fluid-cartridge (B) as shown in FIG. 4(b') of the fluid injecting system (100) in accordance with another embodiment of the present invention. Prior to the injection process, the distal end (M) of the fluid container (50) of the fluid-cartridge (B) is attached at the proximal end (P) of the injector (A) through the inner engagement means (14 b) of the injector body (10) to the engagement means (14 a') of the fluid container (50) to constitute the fluid injecting system (100) as shown in FIG. 8(b).

Figure 8A:
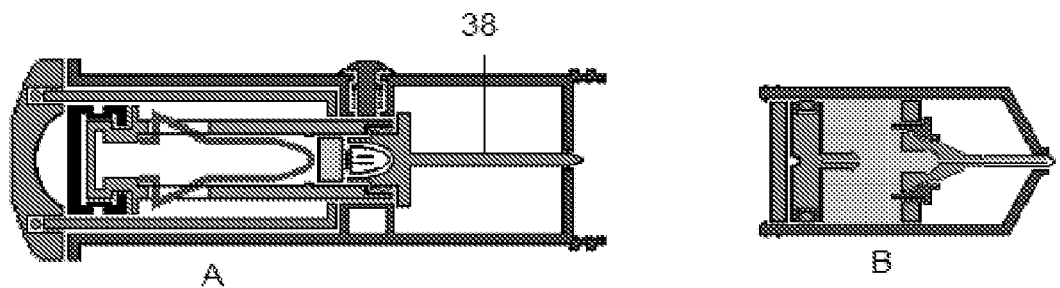
Figure 8B:
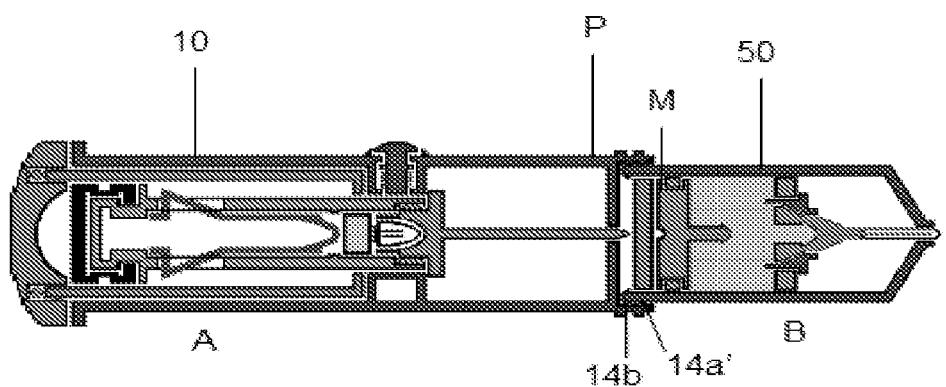
Figure 8C:
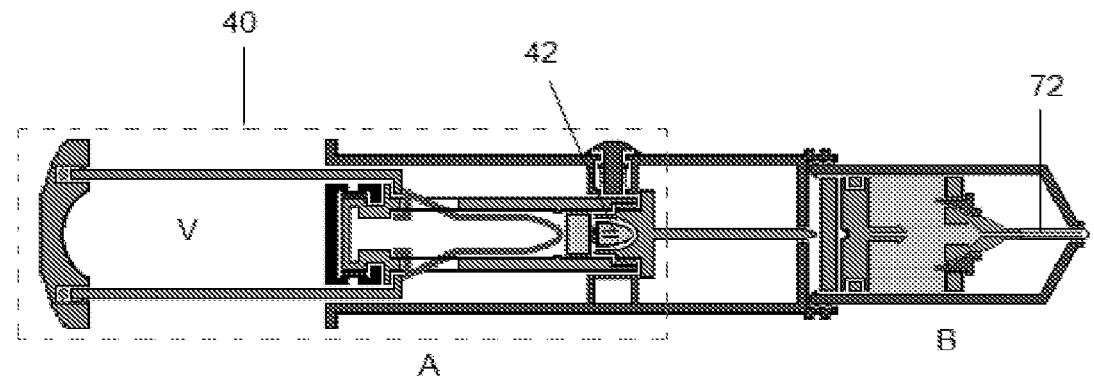
Figure 8D:
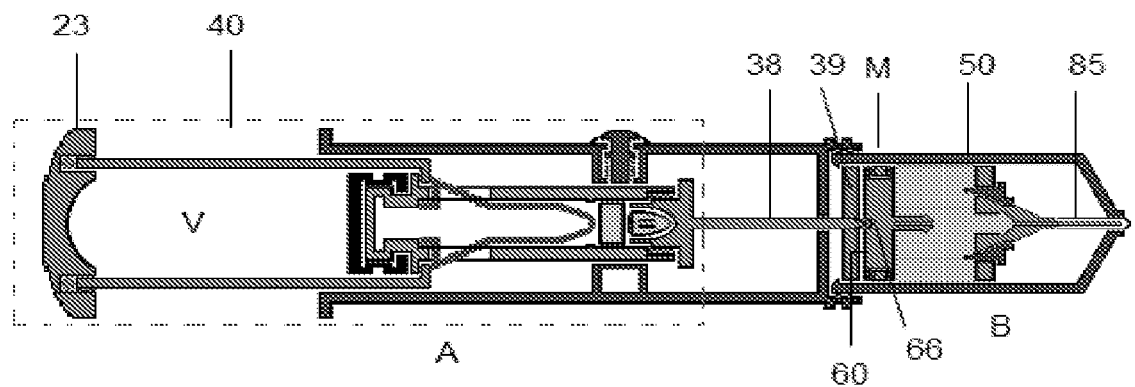
Figure 8E:
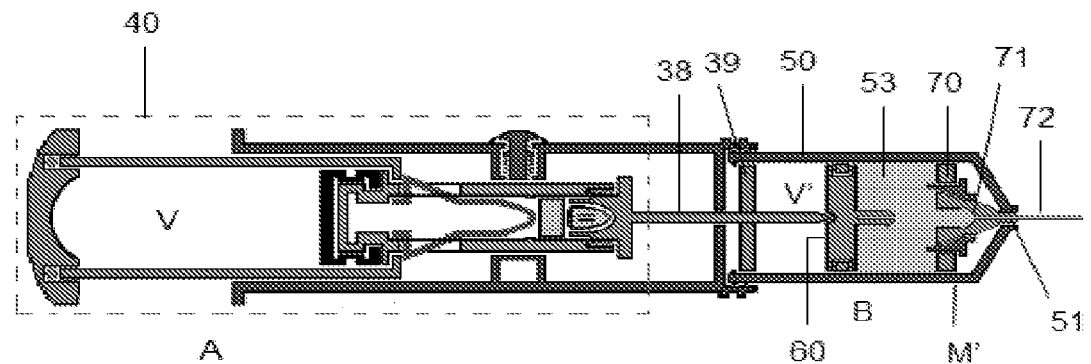

As shown in FIG. 8(c), the LED indicator (42) gets switched on as soon as the outer plunger barrel (22) is pulled out at its full length to constitute the united plunger barrel (40) retaining the vacuum (V) between the inner plunger barrel (21) and the outer plunger barrel (22) and the LED indicator (42) illuminates the end tip of the hypodermic needle (72) and surrounding area of the injectable site. On pushing the united plunger barrel (40) through the thumb-rest (23) the needle shaped plunger shaft (38) pierces the rubber cap (39) provided on the distal end (M) of the fluid-container (50) and gently enters into the conical cavity (66) of the piston assembly (60) as shown in FIG. 8(d). On further pushing the united plunger barrel (40), the needle shaped plunger shaft (38) presses the piston assembly (60) in forward direction, which simultaneously pushes the fluid (53) along with the retractable needle assembly (70) in forward direction until the hypodermic needle (72) extends out through the opened conical mouth (51) of the fluid container (50) and the needle hub (71) settles inside the fluid container (50) at the proximal end (M') of the fluid container (50). As soon as the piston assembly (60) moves in forward direction and goes apart from the rubber cap (39), a vacuum (V') is generated between the piston assembly (60) and the rubber cap (39), as shown in FIG. 8(e). Further, the needle guard (85) is removed from the hypodermic needle (72) to expose the hypodermic needle (72).

Figure 8F:
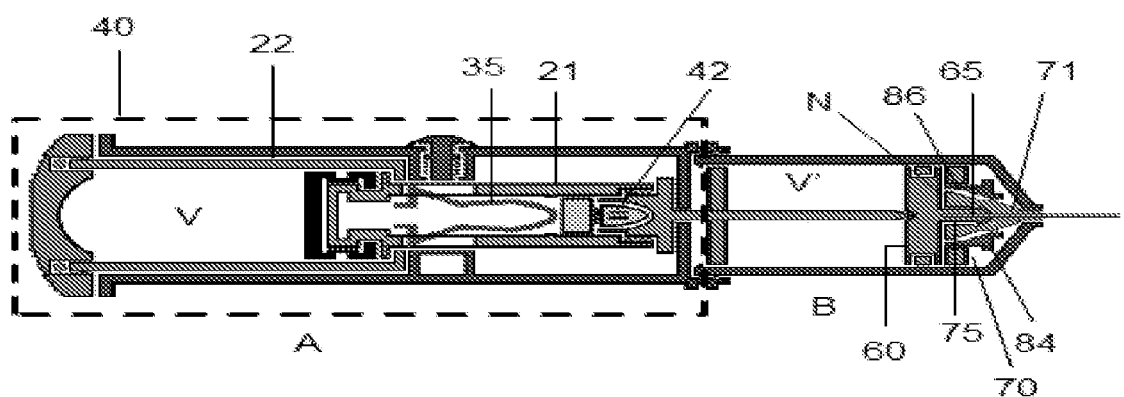
Figure 8G:
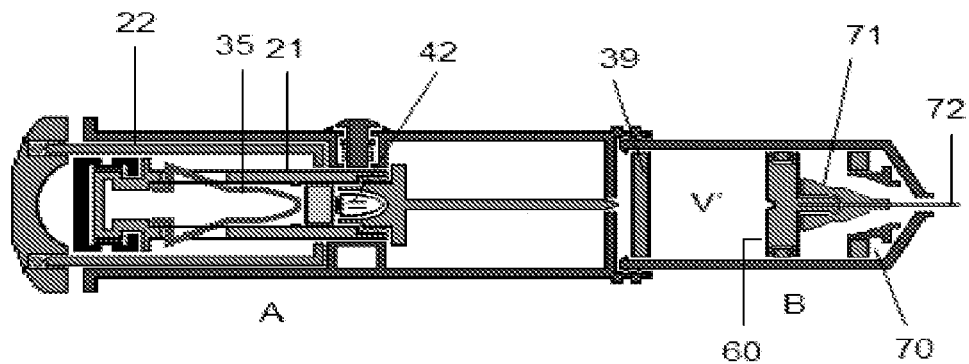

As shown in FIG. 8(f), on further pushing the united plunger barrel (40) in forward direction, the conical cavity (75) of the needle hub (71) attaches with the needle catch projection (65) of the piston assembly (60) of the fluid-cartridge (B). Just before the completion of the injection process, the proximal end (N) of the piston assembly (60) comes in close contact of the end tips of the plurality of horizontally extended pins (86) of the cap (84) holding the needle hub (71), which begins sliding in forward direction and separates the retractable needle assembly (70) from the needle hub (71). At this stage the U-clip locking means (35) of the injector (A) is pressed inwardly which unlocks the inner plunger barrel (21) from the outer plunger barrel (22) and results in backward movement of the inner plunger barrel due to release of the vacuum (V) between the inner plunger barrel (21) and the outer plunger barrel (22) and thereafter, the inner plunger barrel (21) comes at its initial state as shown in FIG. 8(g). As soon as the injection process completes, the LED indicator (42) gets switched off indicating the completion of the injection process.

Figure 8H:
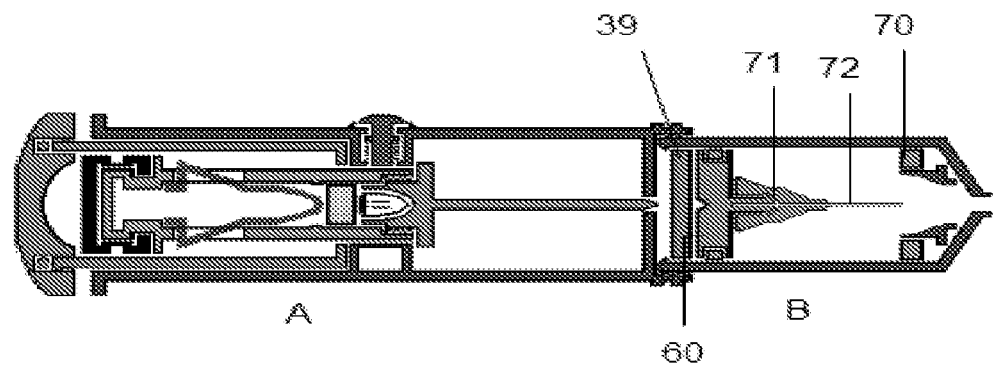

Further, as shown in FIG. 8(g), the vacuum (V') remains between the rubber cap (39) and the piston assembly (60) holding the hypodermic needle (72) even after withdrawal of the needle hub (71) from the retractable needle assembly (70). This vacuum (V') results in retraction of the hypodermic needle (72) along with the piston assembly (60) in backward direction and the hypodermic needle (72) is finally encapsulated within the empty fluid-cartridge (B) as shown in FIG. 8(h).

Figure 8I:
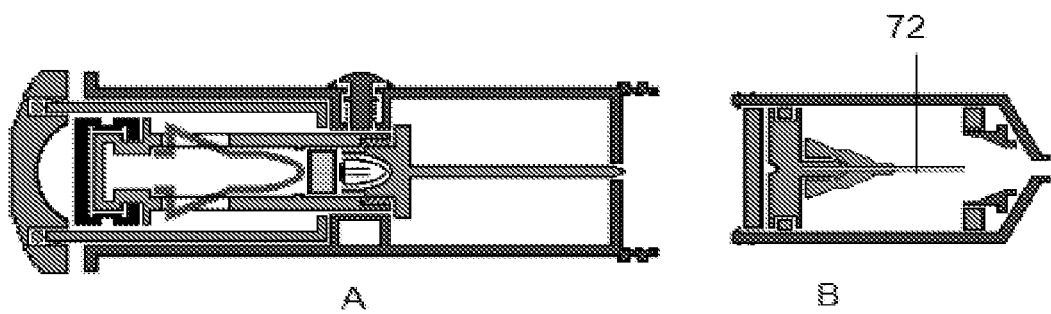

As shown in FIG. 8(i) the empty fluid-cartridge (B) containing encapsulated hypodermic needle (72) is detached from the injector (A) to dispose of safely whereas the injector (A) finally attains its original state to become ready for next operation.

Figure 9A:
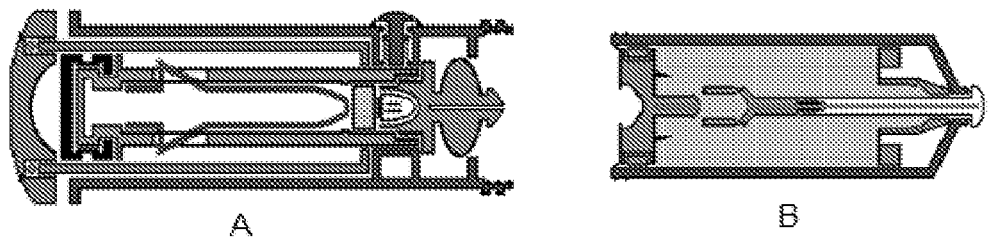
Figure 9B:
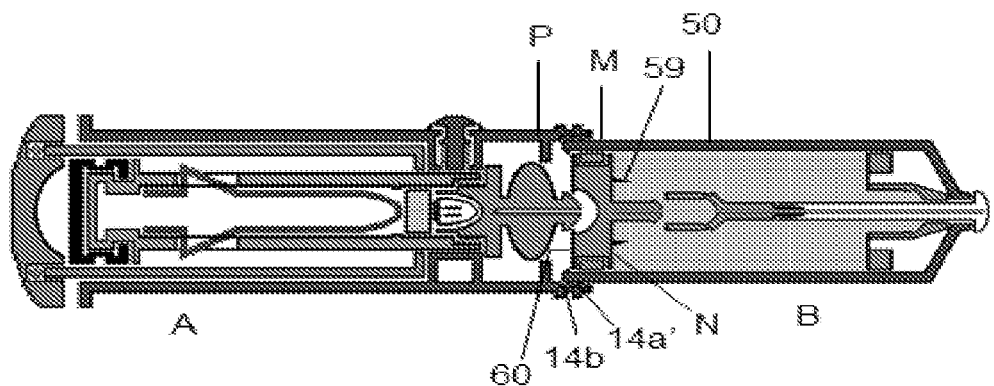
Figure 9C:
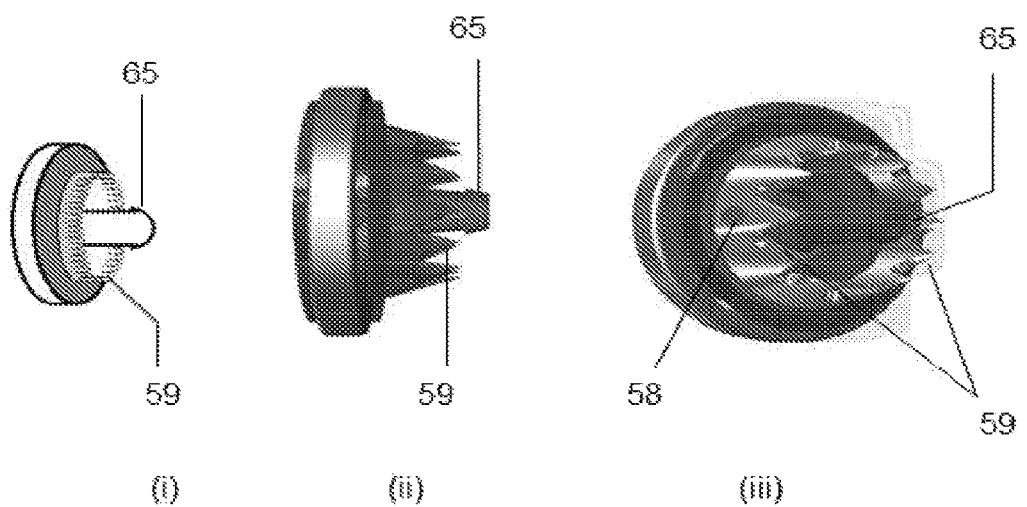

FIG. 9(a) illustrates the injector (A) and the fluid-cartridge (B) as shown in FIG. 5(a) of the fluid injecting system (100) in accordance with yet another embodiment of the present invention. Prior to the injection process, the distal end (M) of the fluid container (50) of the fluid-cartridge (B) is attached at the proximal end (P) of the injector (A) through the inner engagement means (14 b) of the injector body (10) to the engagement means (14 a') of the fluid container (50) to constitute the fluid injecting system (100), as shown in FIG. 9(b). Further, the fluid-cartridge (B) is configured to have the cylindrical saw blade (59) at the proximal end (N) of the piston assembly (60) of the fluid-cartridge (B). The cylindrical saw blade (59) surrounds the needle catch projection (65) of the piston assembly (60) of the fluid-cartridge (B), and is provided with a hole passage (58) as shown in FIG. 9(c) (i), (ii) and (iii).

Figure 9D:
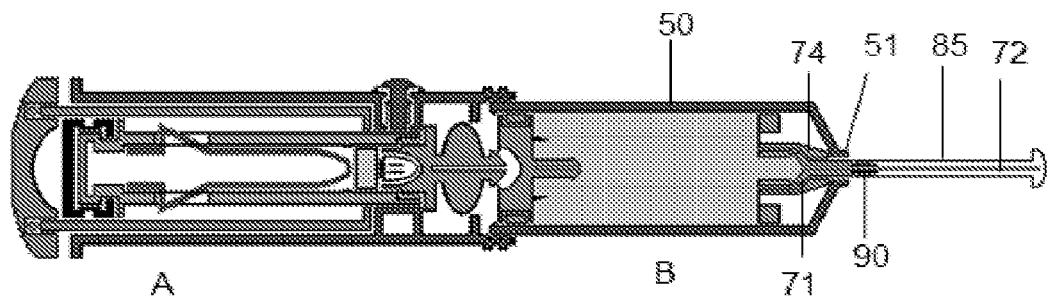
Figure 9E:
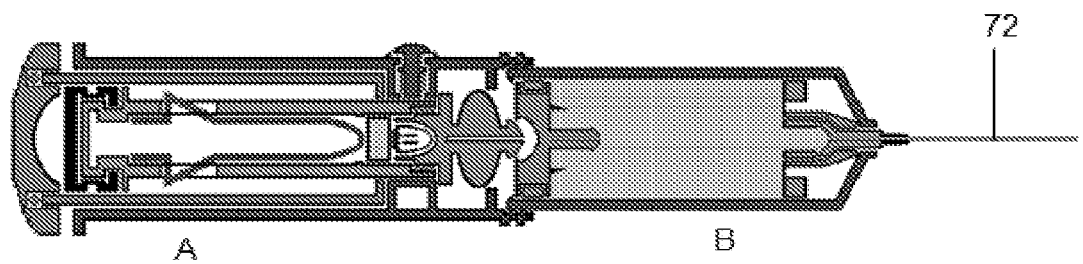

As shown in FIG. 9(d), the needle guard (85) along with the hypodermic needle (72) is drawn out by the user, which facilitates the hypodermic needle (72) along with the needle guard (85) to extend out through the opened conical mouth (51) of the fluid container (50) and the needle holder (74) click fits with the needle hub (71). Thereafter, the needle guard (85) is rotated in the anticlockwise direction by 90 degrees to unlock the locking means (90) and drawn out to remove the needle guard (85) to expose the hypodermic needle (72) as shown in FIG. 9(e).

Figure 9F:
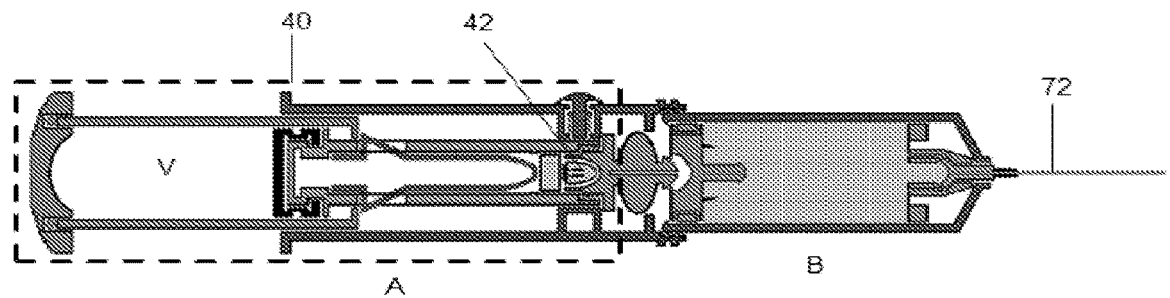
Figure 9G:
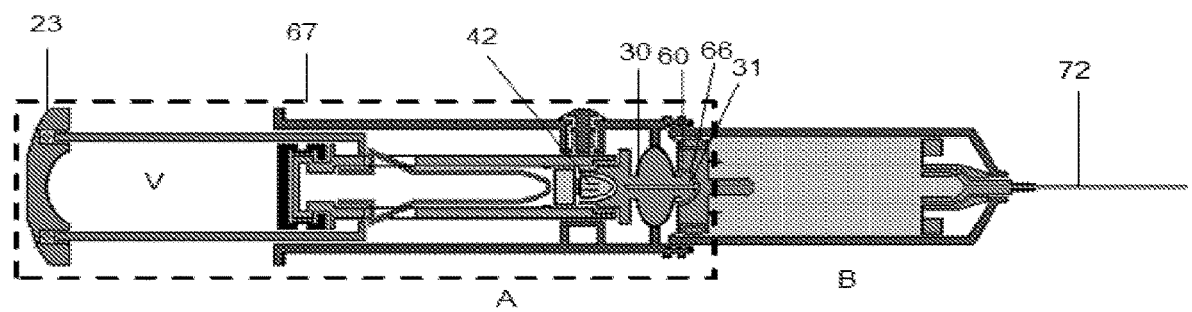

As shown in FIG. 9(f), the LED indicator (42) gets switched on as soon as the vacuum (V) is generated in the united plunger barrel (40) and illuminates the end tip of the hypodermic needle (72) and surrounding area of the injectable site to facilitate injection in dark also. On pushing the united plunger barrel (40) through the thumb-rest (23) the forceps-lock head (31) of the plunger shaft (30) gently enters into the conical cavity (66) of the piston assembly (60) and constitutes the single plunger unit (67) as shown in FIG. 9(g). On further pushing the single plunger unit (67), the piston assembly (60) simultaneously pushes the fluid (53) in forward direction, which is injected into the body through the hypodermic needle (72) as shown in FIG. 9(h).

Figure 9H:
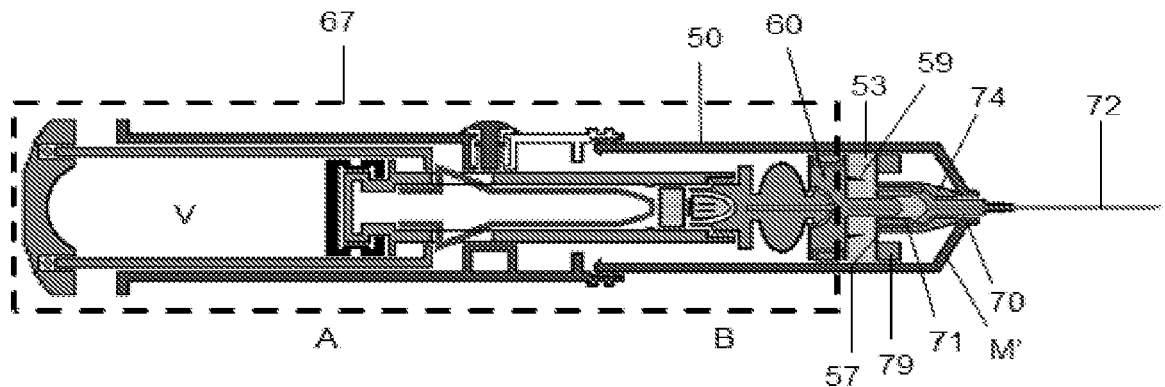

As shown in FIG. 9(h), the circular O-ring (79) having the needle holder (74) at center is provided at the proximal end (M') of the fluid container (50). The circular O-ring (79) is further provided with the thin layer circular diaphragm (57) between the circular O-ring (79) and the needle holder (74). A diameter of an inner-edge of the thin layer circular diaphragm (57) is slightly lesser than an inner diameter of the cylindrical saw blade (59), whereas a diameter of an outer-edge of the thin layer circular diaphragm (57) is slightly greater than an outer diameter of the cylindrical saw blade (59), so that the cylindrical saw blade (59) may conveniently cut the thin layer of circular diaphragm (57) and hold the needle holder (74) firmly at the end of the injection process. Further, the retractable needle assembly (70) comprises the needle hub (71) containing the hypodermic needle (72) encapsulated within the needle guard (85) through the locking means (90).

Figure 9I:
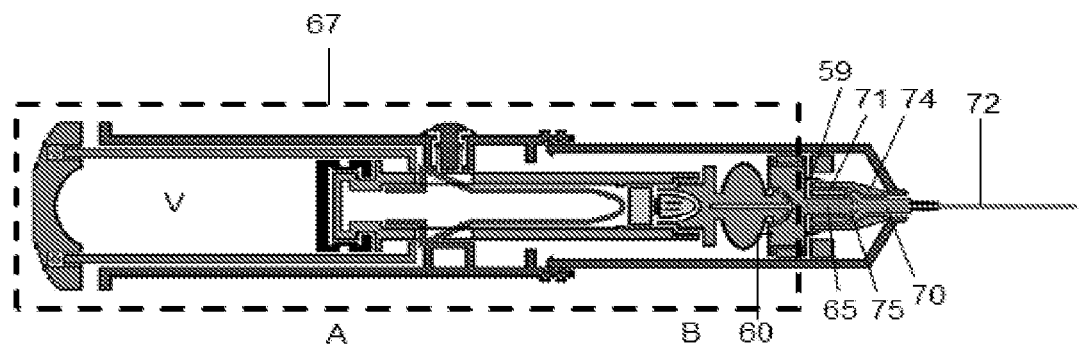
Figure 9J:
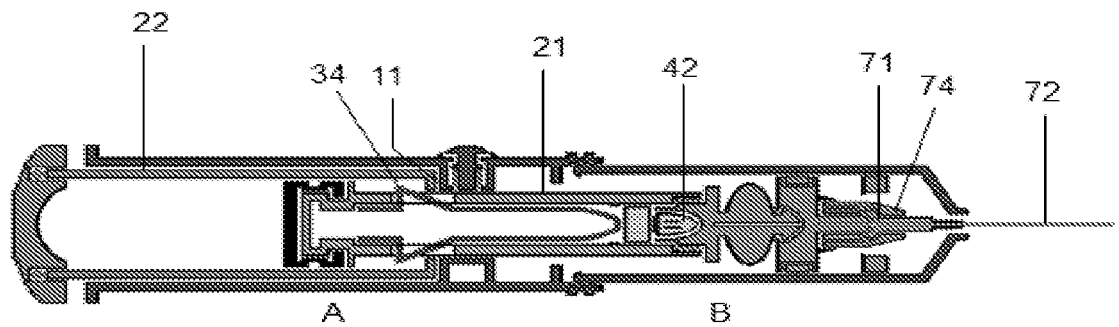

On further pushing the single plunger unit (67) in forward direction, as shown in FIG. 9(i), the cylindrical saw blade (59) cuts the thin layer circular diaphragm (57) and holds the needle holder (74) at the end of the injection process. At the same time, the needle catch projection (65) of the piston assembly (60) also enters into the conical cavity (75) of the needle hub (71) and gets engage therein to attach the retractable needle assembly (70). Simultaneously, the conical lock-notch (34) firmly engaging the outer plunger barrel (22) to the inner plunger barrel (21) itself presses inwardly, while axially passing through passage of the partition ring (11) in forward direction. It unlocks and releases the outer plunger barrel (22) and consequently, the inner plunger barrel (21) moves in backward direction due to reduced pressure of the vacuum (V) between the outer plunger barrel (22) and the inner plunger barrel (21) as shown in FIG. 9(j). Further, the movement of the inner plunger barrel (21) in the backward direction gently retracts the hypodermic needle (72) along with the needle holder (74) holding the needle hub (71) due to the reduced pressure of the vacuum (V).

Figure 9K:
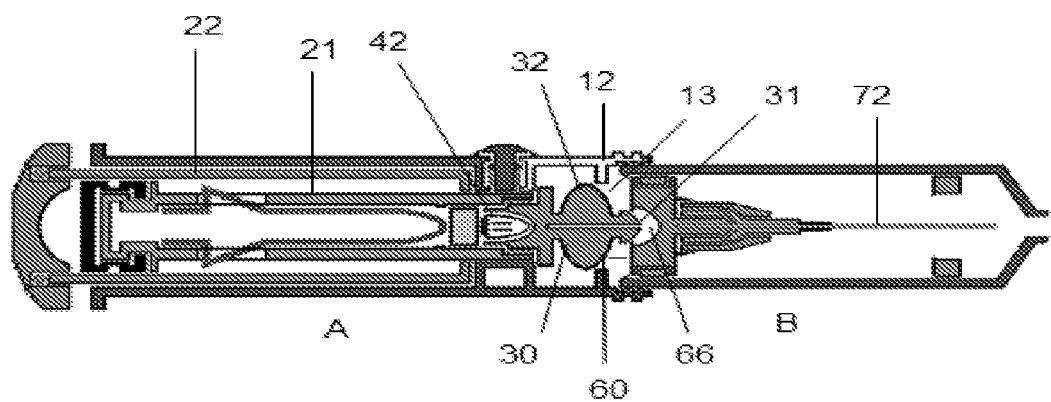

As shown in FIG. 9(k), during the movement of the inner plunger barrel (21) in the backward direction, the flaps (32) pass through the central passage (13) of the flange ring (12) and press inwardly resulting in closure of the forceps-lock head (31), releasing itself from the conical cavity (66) of the piston assembly (60), leaving behind the hypodermic needle (72) encapsulated within the empty fluid-cartridge (B). Thus, the inner plunger barrel (21) along with plunger shaft (30) attains its initial state soon after the vacuum (V) is completely released. As soon as the injection process completes, the LED indicator (42) gets switched off indicating the completion of the injection process.

Figure 9L:
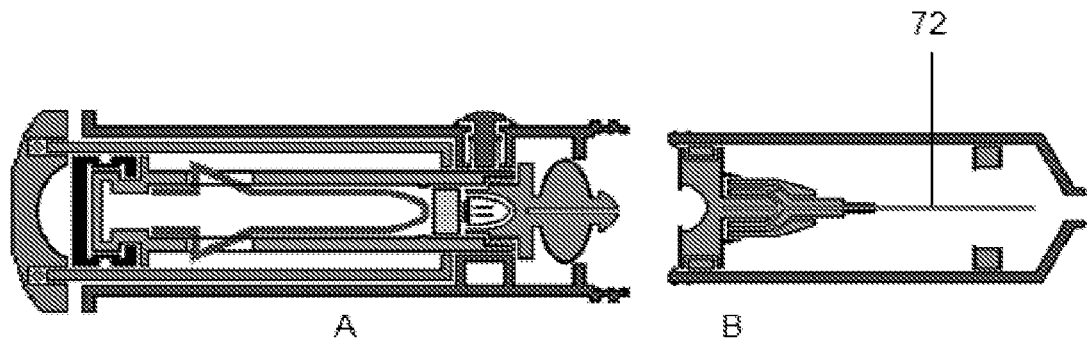
Figure 9M:
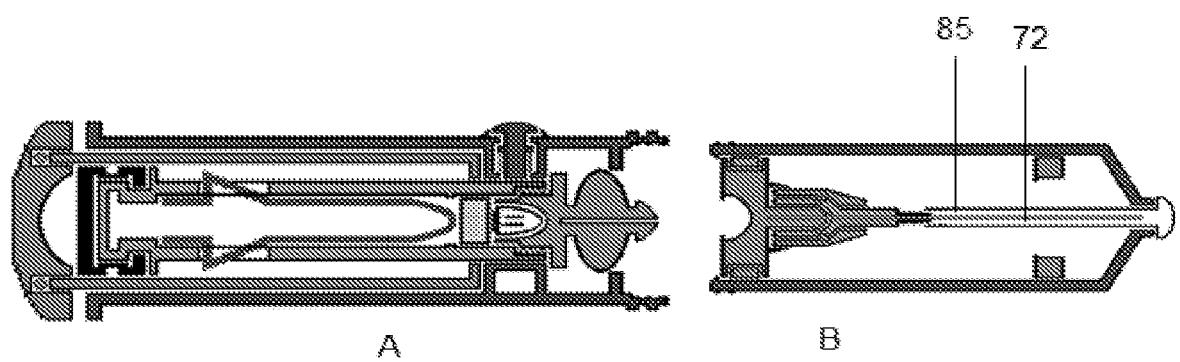

As shown in FIG. 9(l), the empty fluid-cartridge (B) encapsulating the hypodermic needle (72) is detached from the injector (A) to dispose of safely, whereas the injector (A) finally attains its original state to become ready for next operation. Further, the needle guard (85) may be inserted on the retracted hypodermic needle (72) in the empty fluid-cartridge (B), as shown in FIG. 9(m).

FIG. 10 illustrates the injector (A) and the fluid-cartridge (B) as shown in FIG. 6(a) of the fluid injecting system (100) in accordance with yet another embodiment of the present invention. Prior to the injection process, the distal end (M) of the fluid container (50) of the fluid-cartridge (B) is attached at the proximal end (P) of the injector (A) through the inner engagement means (14 b) of the injector body (10) to the engagement means (14 a') of the fluid container (50) to constitute the fluid injecting system (100).

As shown in FIG. 10, the piston assembly (60) of the fluid-cartridge (B) is configured to have a circular ridge projection (64) at rim of the piston flange (61) at a proximal end (Q) of the piston flange (61) of the piston assembly (60). The circular ridge projection (64) is having a width equal to a width of the O-ring (79) of the retractable needle assembly (70) at a distal end (S') of the O-ring (79). The needle holder (74) of the retractable needle assembly (70) is provided with a flange rim (54) which is further provided with a collar projection (55) at a distal end (X') of the needle holder (74) to hold the O-ring (79) firmly between the flange rim (54) and the interior of the fluid container (B). The O-ring (79) is having a width, inner and outer diameter at the distal end (S') equal to the width, inner and outer diameter of the circular ridge projection (64) at a proximal end (W) of the circular ridge projection (64). Also, the inner diameter of the O-ring

(79) at a proximal end (W') of the O-ring (79) is greater than the inner diameter of the O-ring at the distal end (S') of the O-ring (79) to allow convenient seating of the O-ring (79) around the collar projection (55) of the flange rim (54). Further, the operation of the fluid injecting system (100) has been described in earlier embodiments and therefore, the same has not been discussed here for the sake of brevity. Furthermore, the retraction mechanism of the hypodermic needle (72) is different from the other embodiments in which just before the completion of the injection process, the circular ridge projection (64) pushes the O-ring (79) in forward direction to disengage the O-ring (79) from the flange rim (54) of the needle holder (74) resulting in release of the needle holder (74). Thereafter, movement of the inner plunger barrel (21) in the backward direction, as explained in previous embodiments, gently retracts the hypodermic needle (72) along with the needle holder (74) holding the needle hub (71) in the empty fluid-cartridge (B) due to the reduced pressure of the vacuum (V). Also, the injector (A) finally attains its original state to become ready for next operation.

FIG. 11 illustrates a perspective view of a fluid collector (200) in accordance with an embodiment of the present invention. As shown in FIG. 11, the fluid collector (200) comprises a fluid container (50'), a piston assembly (60') and a container cover (80). Further, the fluid collector (200) is releasably engaged with the injector (A) at the proximal end (P) of the injector (A).

In accordance with an embodiment of the present invention, the fluid container (50') is a uniformly regular and hollow cylindrical body having a centrally extended conical projection (70') containing a needle holder (71') at a proximal end (C') of the conical projection (70') to hold a detachable hypodermic needle (72'). A distal end (E') of the fluid container (50') is covered with a thin layer of diaphragm (52). Further, the fluid container (50') is provided with engagement means (14 a", 14 b") at the distal end (E') to firmly engage with the inner engagement means (14 b) and the outer engagement means (14 a) provided at the proximal end (P') of the injector body (10).

In accordance with an embodiment of the present invention, the piston assembly (60') comprises a piston flange (61') provided with a conical cavity (66') at center of the piston assembly (60') at a distal end (D') of the piston assembly (60') to receive and retain the forceps-lock head (31) of the plunger shaft (30) of the injector (A) during the fluid collection process. The thin layer of diaphragm (52) of the fluid container (50') is pierced by the forceps-lock head (31) and thereafter the forceps-lock head (31) enters into the conical cavity (66') of the piston assembly (60'). The conical cavity (66') is having an opening diameter lesser than an inner diameter of the conical cavity (66') to receive and firmly engage with the opened forceps-lock head (31) of the plunger shaft (30) of the injector (A). Further, the opening diameter of the conical cavity (66') is greater than an outer diameter of the closed forceps-lock head (31) of the plunger shaft (30) to receive the closed forceps-lock head (31) conveniently. Also, a rim of the piston flange (61') is provided with a plurality of grooves (62') to hold a piston seal (63') between the piston flange (61') and the fluid container (50').

In accordance with an embodiment of the present invention, the container cover (80) is a uniformly regular and hollow cylindrical body having an open mouth at a distal end (F'). The container cover (80) is having an internal diameter slightly higher than an outer diameter of the fluid container (50') at a proximal end (G') of the fluid container (50') to firmly hold the fluid container (50') to fixedly cover it. Further, the container cover (80) is internally provided with a concave diaphragm (81) in middle of the container cover (80) facing towards the open mouth at the distal end (F') of the container cover (80). Furthermore, the container cover (80) is removably attached with the fluid container (50'). The concave diaphragm (81) is having a central hole (82) at center of the concave diaphragm (81). The central hole (82) is configured to have a diameter less than a detachable needle hub (78).

In accordance with an embodiment of the present invention, the concave diaphragm (81) is divided into a plurality of equal parts constituting respective number of flaps, which are configured to be pressed only towards bottom of the container cover (80) to increase size of the central hole (82) to allow entry of a rim of the detachable hypodermic needle (72'). Further, the central hole (82) does not allow the detachable hypodermic needle (72') to retract in backward direction.

In accordance with an embodiment of the present invention, the container cover (80) is firmly attached with the fluid container (50') by way of a removable ring seal (83) between the fluid container (50') and the container cover (80) to cover the proximal end (G') of the fluid container (50').

The schematic details of operation of the fluid collector (200) coupled with the injector (A) are shown in FIG. 12(a) to FIG. 12(o).

FIG. 12(a) illustrates the fluid collector (200) and the injector (A) in accordance with an embodiment of the present invention. Prior to the fluid collection process, the fluid collector (200) is conveniently attached at the proximal end (P) of injector (A) through the engagement means (14 a") provided at the distal end (E') of the fluid container (50') to firmly engage with the inner engagement means (14 b) provided at the proximal end (P') of the injector body (10) to constitute a united assembly of the injector (A) and the fluid collector (200) as shown in FIG. 12(b). Further, the removable ring seal (83) is removed from the fluid container (50') as shown in FIG. 12(c).

As shown in FIG. 12(d), the outer plunger barrel (22) of the injector (A) is withdrawn in backward direction unless the interiorly protruded flange rim (24) passes over the conical lock-notch (34) of the U-clip locking means (35) and gets engage at the distal end (G) of the inner plunger barrel (21) to combine the inner plunger barrel (21) and the outer plunger barrel (22) in order to constitute the united plunger barrel (40). During this process, the vacuum (V) is generated between the inner plunger barrel (21) and the outer plunger barrel (22). The LED indicator (42) gets switched on as soon as the vacuum (V) is generated in the united plunger barrel (40) and illuminates the end tip of the hypodermic needle (72).

As shown in FIG. 12(e), the container cover (80) is removed from the fluid container (50') and thereafter, the detachable hypodermic needle (72') is pierced conveniently into a source of fluid or the target.

Figure 12:
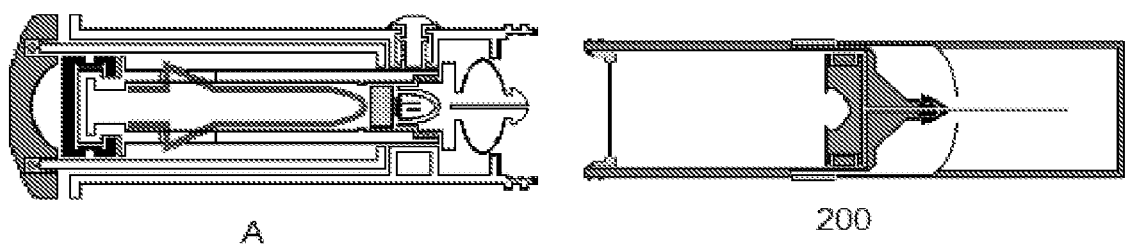
Figure 12:
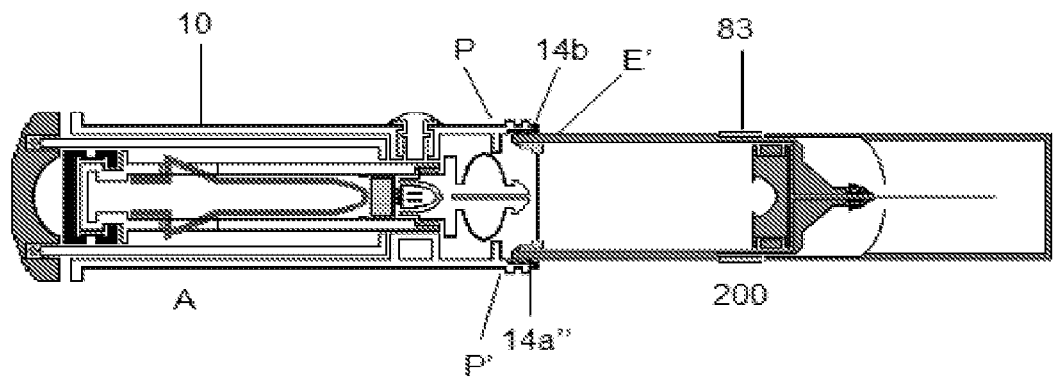
Figure 12:
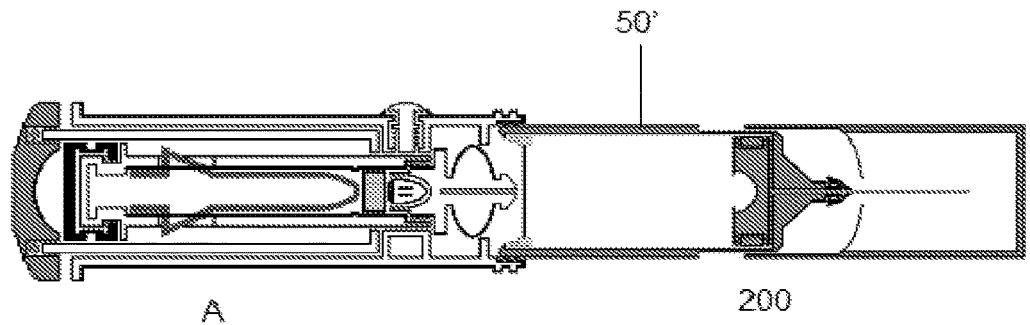
Figure 12:
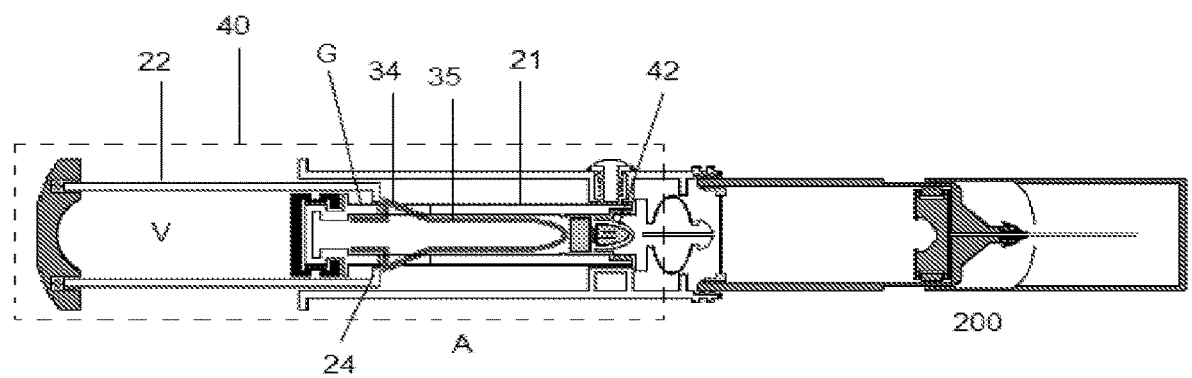
Figure 12:
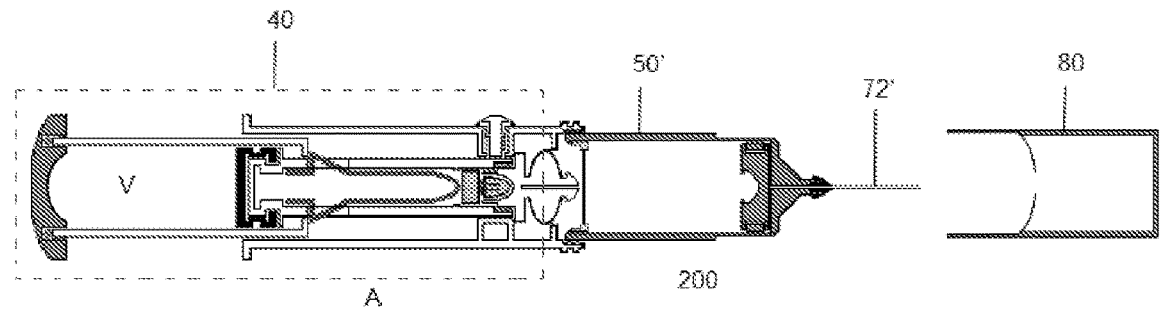
Figure 12:
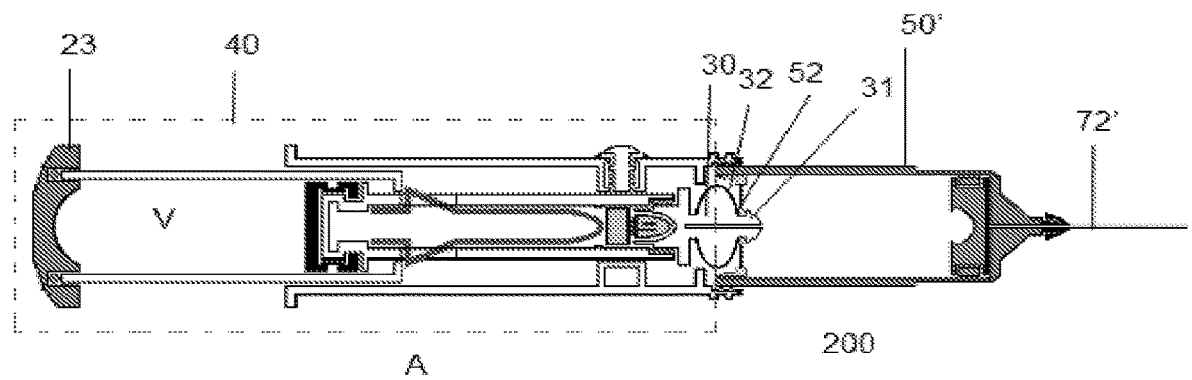
Figure 12:
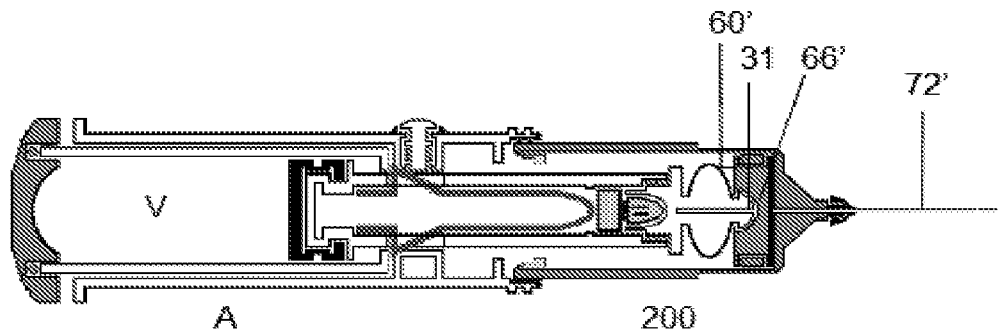
Figure 12:
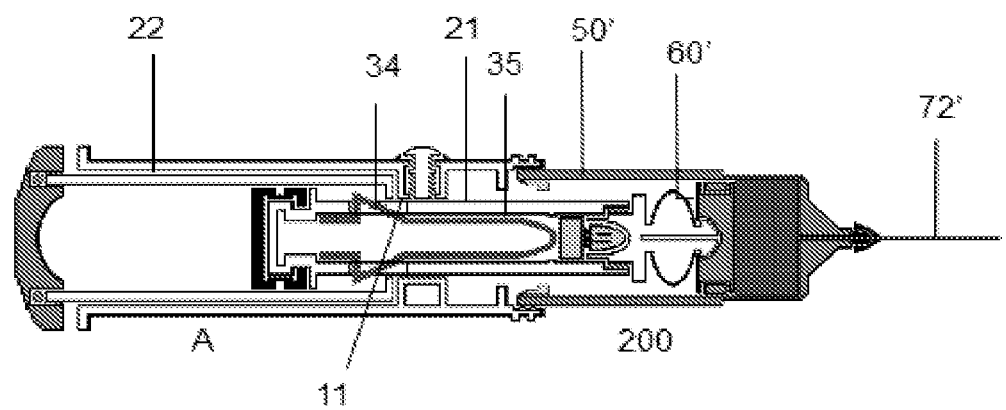
Figure 12:
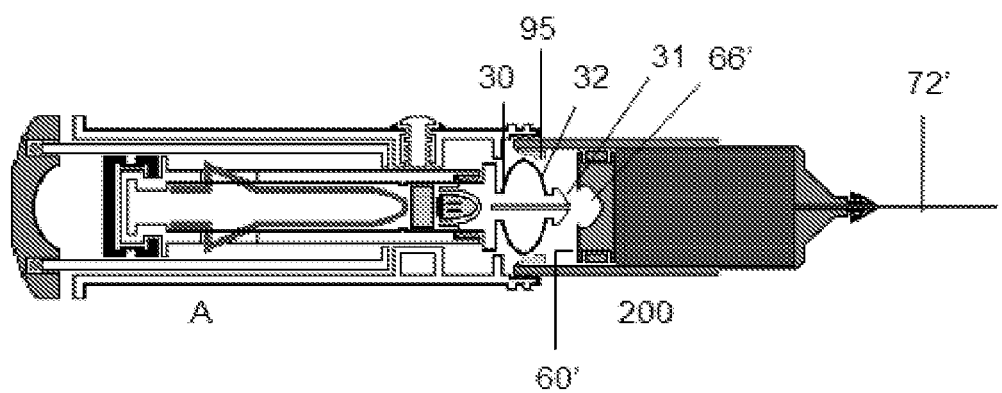
Figure 12:
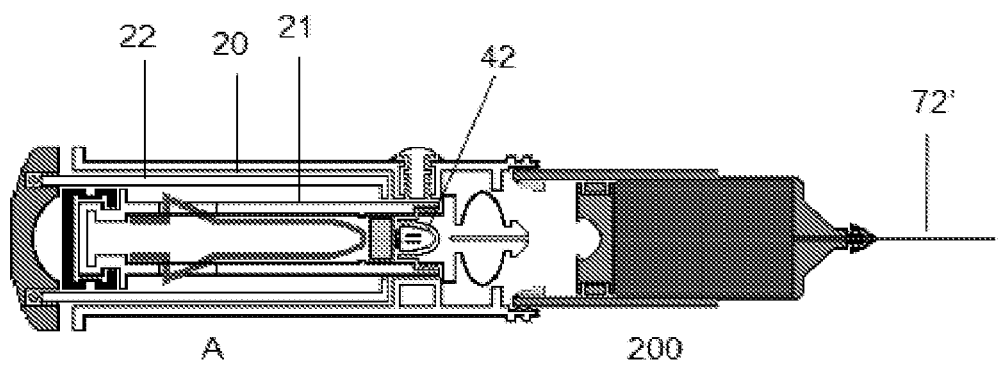
Figure 12:
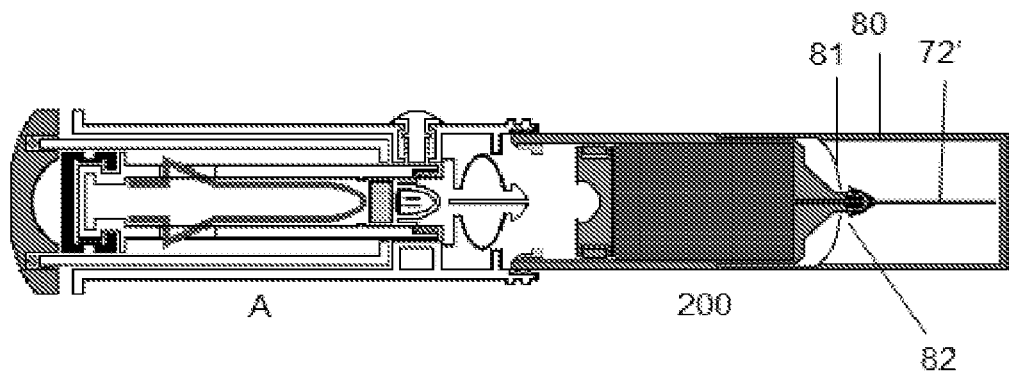
Figure 12:
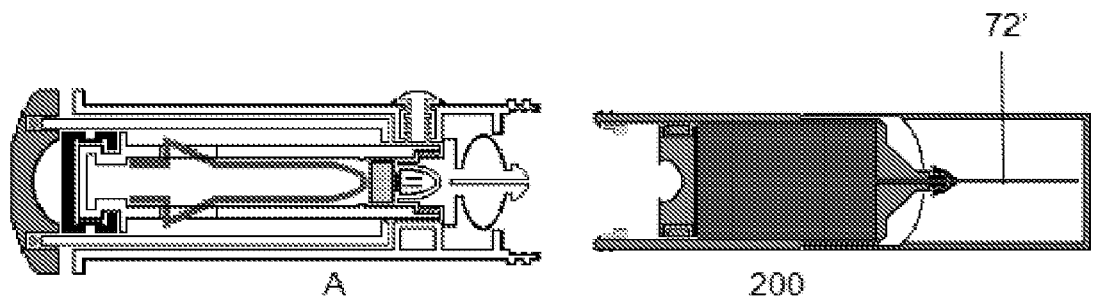
Figure 12:
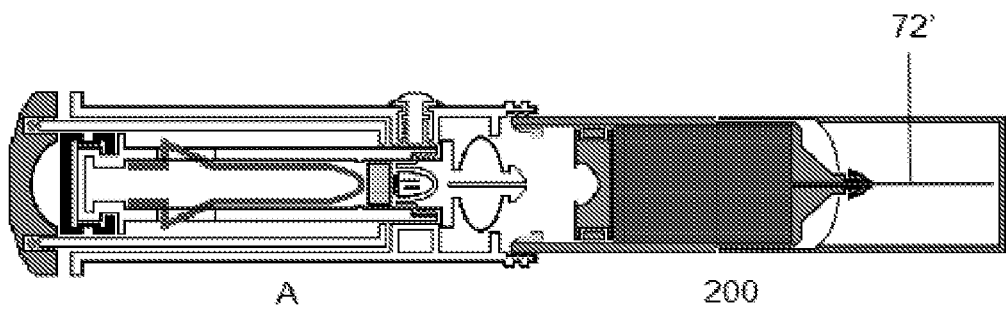
Figure 12:
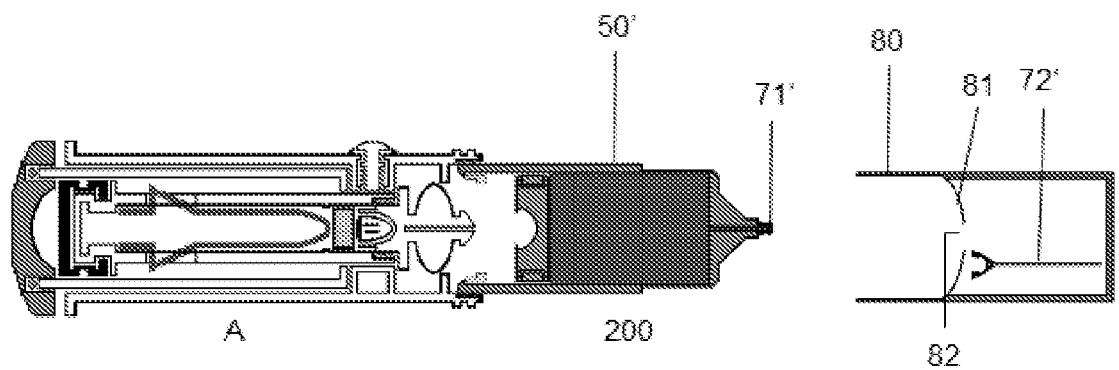
Figure 12:
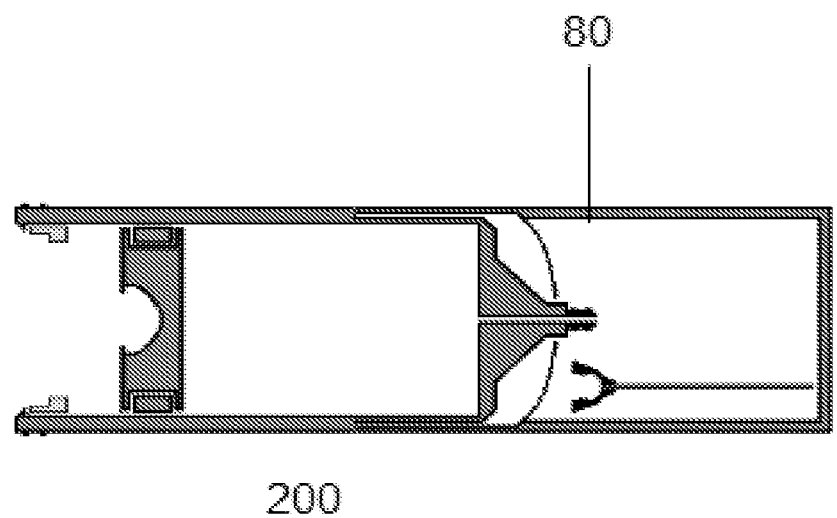

As shown in FIG. 12(f), the united plunger barrel (40) is pushed in forward direction through the thumb-rest (23) due to which the forceps-lock head (31) of the plunger shaft (30) of the injector (A) gently enters into the fluid collector (200) piercing through the thin layer of diaphragm (52) of the fluid container (50') with the help of sharp-edged blades provided at the proximal end (K') of the flaps (32). After piercing the thin layer of diaphragm (52) the forceps-lock head (31) enters into the conical cavity (66') of the piston assembly (60'), where the forceps-lock head (31) is firmly retained by the conical cavity (66') as shown in FIG. 12(g). At this stage, the conical lock-notch (34) of the U-clip locking means (35) firmly engaging the outer plunger barrel (22) with the inner plunger barrel (21) itself presses inwardly while axially passing through the passage of the partition ring (11) in forward direction. It unlocks and releases the outer plunger barrel (22) and facilitates retraction of the inner plunger barrel (21) along with the piston assembly (60') of the fluid collector (200) resulting in aspiration of the fluid from the source of the fluid through the passage of detachable hypodermic needle (72') and collects the fluid into the fluid container (50') as shown in FIG. 12 (h).

As shown in FIG. 12(i), when the flaps (32) of the plunger shaft (30) pass through a flange ring (95) containing the thin layer of diaphragm (52), the forceps-lock head (31) gets closed being pressed inwardly resulting in detachment of the forceps-lock head (31) from the conical cavity (66') of the piston assembly (60') of the fluid collector (200). Thus, a fixed volume of the fluid is stored in the fluid collector (200). As soon as the vacuum (V) between the inner plunger barrel (21) and the outer plunger barrel (22) is completely released, the inner plunger barrel (21) attains its initial original position to fold the united plunger barrel (40), as shown in FIG. 12(j). As soon as the fluid collection process completes, the LED indicator (42) gets switched off indicating the completion of the fluid collection process.

The push-button (43) of the injector (A) may be used to regulate, control or restrict the movement of retracting united plunger barrel (40) under the influence of the reduced pressure between the inner plunger barrel (21) and the outer plunger barrel (22). On pressing the push-button (43), it restricts the movement of the united plunger barrel (40) in backward direction and allows the retraction when the push-button (43) is left un-pressed.

As shown in FIG. 12(k), the detachable hypodermic needle (72') is gently withdrawn from the source of fluid and is covered by the container cover (80). While covering with the container cover (80), rim of the detachable hypodermic needle (72') presses the flaps of the concave diaphragm (81) in forward direction to increase diameter of the central hole (82), so as to allow passage of the detachable hypodermic needle rim across the central hole (82). On completion of covering process, the flaps of concave diaphragm (81) retain initial state. The fluid collector (200) containing the fluid may now be conveniently separated from the injector (A) as shown in FIG. 12(l).

In accordance with an embodiment of the present invention, the fluid stored in the fluid collector (200) is further processed. For the processing of the fluid, the collected fluid needs be withdrawn from the fluid collector (200) which is conveniently and efficiently performed by the injector (A) itself.

As shown in FIG. 12(m), the fluid collector (200) containing the stored fluid is again attached with the injector (A). Further, the attachment of the fluid collector (200) and the injector (A) has been described earlier and therefore, the same has not been discussed here for the sake of brevity.

As shown in FIG. 12(n), the container cover (80) is removed by drawing out it in forward direction. During this process, the detachable hypodermic needle (72') is detached and separated from the detachable needle holder (71') as diameter of the central hole (82) of concave diaphragm (81) being lesser than the rim of the detachable hypodermic needle (72') does not allow the detachable hypodermic needle (72') to move in backward direction and results in detachment of the detachable hypodermic needle (72') from the fluid container (50'). The detachable hypodermic needle (72') finally and safely remains inside the container cover (80) and becomes non-reusable. Further, a fresh hypodermic needle may be attached with the fluid container (50') to repeat the whole process to liberate out the fluid contents in desired volume as per the requirements.

As shown in FIG. 12(o), after complete discharging of the fluid from the fluid collector (200), empty fluid collector (200) may again be covered by fixing the container cover (80) to safely dispose-off the empty fluid collector (200) after detaching it from the injector (A).

A uniform cylindrical hollow barrel ring (49) of appropriate length, as shown in FIG. 13(a) may be inserted in the fluid collector (200) through the distal end (E') of the fluid container (50') to ensure collection of predefined volume of the fluid. An outer diameter of the cylindrical hollow barrel ring (49) is equal to the inner diameter of the fluid container (50'), whereas an inner diameter of the cylindrical hollow barrel ring (49) is equal to an inner diameter of the flange ring (12) of the injector (A). Further, length of the cylindrical hollow barrel ring (49) is lesser than the length of the fluid contained as per the requirement needed to collect the appropriate/desired pre-defined volume of the fluid. On inserting the cylindrical hollow barrel ring (49) in the fluid container (50') through the distal end (E'), it slides the flange ring (95) containing the thin layered diaphragm (52) in forward direction to reduce space in the fluid container (50') to collect the pre-defined volume of the fluid as shown in FIGS. 13 (b) and (c).

FIG. 14 is a flow chart illustrating a fluid injecting method (300) in accordance with an embodiment of the present invention.

At step 302, as shown in FIG. 14, the fluid-cartridge (B) having the fluid (53) sandwiched between the piston assembly (60) and the retractable needle assembly (70) of the fluid-cartridge (B) is provided. Further, the fluid (53) is an injectable fluid.

At step 304, the fluid-cartridge (B) is reversibly coupled with the injector (A) having the plunger shaft (30) and the united plunger barrel (40). Also, the injector (A) is having the inner plunger barrel (21) slidable within the outer plunger barrel (22). Further, the fluid-cartridge (B) is reversibly coupled with the injector (A) at the proximal end (P) of the injector (A).

In accordance with an embodiment of the present invention, the united plunger barrel (40) is formed by pulling out the outer plunger barrel (22) completely. Further, the united plunger barrel (40) is configured to retain the vacuum (V) between the inner plunger barrel (21) and the outer plunger barrel (22).

In other words, the outer plunger barrel (22) is pulled out at its full length which results in a reversible engagement of the outer plunger barrel (22) with the locking means (35) of the inner plunger barrel (21) and restricts movement of the outer plunger barrel (22) in the forward direction and forms the united plunger barrel (40).

In accordance with an embodiment of the present invention, the injector (A) is configured for actuating an axial movement of the plunger shaft (30) in the forward direction and in a backward direction for retracting the plunger shaft (30).

At step 306, the united plunger barrel (40) is pushed in the forward direction to deliver the fluid (53) from the fluid-cartridge (B) into the injectable site. Further, the retractable needle assembly (70) of the fluid-cartridge (B) is retracted within the empty fluid-cartridge (B) due to release of the vacuum (V) after completion of the injection process.

In accordance with an embodiment of the present invention, the movement of the inner plunger barrel (21) in the backward direction gently retracts the retractable needle assembly (70) into the empty fluid-cartridge (B) and thereafter, the inner plunger barrel (21) attains its initial state.

FIG. 15 is a flow chart illustrating a fluid collecting method (400) in accordance with an embodiment of the present invention.

At step 402, the fluid collector (200) having the piston assembly (60') and the detachable hypodermic needle (72') is provided. Further, the detachable hypodermic needle (72') is covered by the container cover (80).

At step 404, the fluid collector (200) is reversibly coupled with the injector (A). The injector (A) is having the plunger shaft (30) and the united plunger barrel (40). Also, the injector (A) is having the inner plunger barrel (21) slidable within the outer plunger barrel (22). Further, the fluid collector (200) is reversibly coupled with the injector (A) at the proximal end (P) of the injector (A).

In accordance with an embodiment of the present invention, the united plunger barrel (40) is formed by pulling out the outer plunger barrel (22) completely. Further, the united plunger barrel (40) is configured to retain the vacuum (V) between the inner plunger barrel (21) and the outer plunger barrel (22).

In accordance with an embodiment of the present invention, the injector (A) is configured for actuating the axial movement of the plunger shaft (30) in the forward direction and in the backward direction for retracting the plunger shaft (30).

At step 406, the container cover (80) is removed from the fluid collector (200) to expose the detachable hypodermic needle (72').

In accordance with an embodiment of the present invention, the removable ring seal (83) is removed from the fluid collector (200) in order to separate the container cover (80) from the fluid collector (200).

At step 408, the detachable hypodermic needle (72') is inserted into a target fluid source.

In accordance with an embodiment of the present invention, the step 408 further comprises a step of pushing the united plunger barrel (40) in the forward direction to attach the plunger shaft (30) of the injector (A) with the piston assembly (60') of the fluid collector (200).

At step 410, the fluid from the target fluid source is collected into the fluid collector (200).

In accordance with an embodiment of the present invention, the release of the vacuum (V) results in the backward movement of the inner plunger barrel (21) along with the plunger shaft (30) and the piston assembly (60') which leads to the suction of the fluid from the target fluid source through the passage of detachable hypodermic needle (72') and collects the fluid into the fluid collector (200).

The above-mentioned fluid injecting system and method thereof overcomes the problems and shortcomings of the existing hypodermic syringes having retractable needles and provides a number of advantages over them. The fluid injecting system is having the injector and the fluid-cartridge and is capable of retracting the hypodermic needle by virtue of self-generated vacuum and encapsulates the hypodermic needle in retracted position within the fluid-cartridge after completion of the injection process. Further, the fluid-cartridge encapsulating the retracted needle becomes non-reusable. Also, the injector of the fluid injecting system is reusable. The fluid injecting system is economical and user friendly and avoids applying additional force to activate the retraction mechanism for retraction of the hypodermic needle. The retraction of the hypodermic syringe may be performed with or without the first spring. In addition, the proposed fluid injecting system provides an advantage of performing the injection process in dark also and patients will also be aware of the injection process as the LED indicator gets switched off after the completion of the injection process.

The exemplary implementation described above is illustrated with specific shapes, dimensions, and other characteristics, but the scope of the invention includes various other shapes, dimensions, and characteristics. Also, the fluid injecting system as described above could be designed and fabricated in various other ways and could include various other materials and various other fluid-cartridge, fluid container, hypodermic needle etc.

Various modifications to these embodiments are apparent to those skilled in the art from the description and the accompanying drawings. The principles associated with the various embodiments described herein may be applied to other embodiments.

Therefore, the description is not intended to be limited to the embodiments shown along with the accompanying drawings but is to be providing broadest scope of consistent with the principles and the novel and inventive features disclosed or suggested herein. Accordingly, the invention is anticipated to hold on to all other such alternatives, modifications, and variations that fall within the scope of the present invention and appended claims.

The invention claimed is:

1. A fluid collector configured to releasably engage with an injector, the fluid collector comprising:
    a fluid container configured to have a centrally extended conical projection containing a detachable needle holder at a proximal end of said conical projection to hold a detachable hypodermic needle;
    a piston assembly having a piston flange provided with a conical cavity at center of said piston assembly at a distal end of said piston assembly to couple a plunger shaft of said injector;
    a container cover being internally provided with a concave diaphragm having a central hole to allow entry of said detachable hypodermic needle along with a detachable needle hub;
    wherein said container cover is removably attached with said fluid container;
    wherein said fluid container is provided with engagement means at a distal end to engage with said injector;
    wherein a united plunger barrel of said injector retaining a vacuum is pushed completely in forward direction to attach said plunger shaft with said conical cavity of said piston assembly; and
    wherein release of said vacuum results in backward movement of an inner plunger barrel of said united plunger barrel along with said piston assembly and in suction of a fluid from a target in said fluid container.

2. The fluid collector as claimed in claim 1, wherein said fluid container comprises a thin layer of diaphragm at said distal end of said fluid container.

3. The fluid collector as claimed in claim 1, wherein said piston flange is configured to have a plurality of grooves to hold a piston seal between said piston flange and said fluid container.

4. The fluid collector as claimed in claim 1, wherein said container cover is having an internal diameter higher than an outer diameter of said fluid container at a proximal end of said fluid container to attach with said fluid container.

5. The fluid collector as claimed in claim 4, wherein said container cover is attached with said fluid container by way of a removable ring seal to cover said proximal end of said fluid container.

6. The fluid collector as claimed in claim 1, wherein said concave diaphragm is provided in middle of said container cover.

7. The fluid collector as claimed in claim 1, wherein said central hole is configured to have a diameter less than said detachable needle hub.

8. The fluid collector as claimed in claim 1, wherein said concave diaphragm is divided into a plurality of equal parts which are configured to be pressed only towards bottom of said container cover to increase size of said central hole to allow entry of said detachable hypodermic needle along with said detachable needle hub.

\* \* \* \* \*